(12) United States Patent
Gokaraju et al.

(10) Patent No.: US 7,625,947 B2
(45) Date of Patent: Dec. 1, 2009

(54) ANALOGS OF 3-O-ACETYL-11-KETO-β-BOSWELLIC ACID

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Trimurtulu Golakoti, Andhra Pradesh (IN)

(73) Assignee: Laila Nutraceuticals, Andhra Pradesh (IN)

( * ) Notice: Subject to any disclaimer, the term of this patent is extended or adjusted under 35 U.S.C. 154(b) by 458 days.

(21) Appl. No.: 10/540,257

(22) PCT Filed: Jun. 18, 2004

(86) PCT No.: PCT/IN2004/000176

§ 371 (c)(1),
(2), (4) Date: Jun. 22, 2005

(87) PCT Pub. No.: WO2005/123649

PCT Pub. Date: Dec. 29, 2005

(65) Prior Publication Data

US 2006/0089409 A1    Apr. 27, 2006

(51) Int. Cl.
A61K 31/21 (2006.01)
A61K 31/015 (2006.01)
C07C 69/74 (2006.01)

(52) U.S. Cl. .............................. 514/510; 514/766; 560/6
(58) Field of Classification Search ................. 514/198, 514/510, 766; 518/170, 171, 554; 560/6
See application file for complete search history.

(56) References Cited

U.S. PATENT DOCUMENTS 6,174,876 B1 *  1/2001  Simmet et al. ............... 514/198
6,534,086 B1    3/2003  Krumhar
6,589,516 B1    7/2003  Eyre et al.

FOREIGN PATENT DOCUMENTS

JP             04288095      * 10/1992

OTHER PUBLICATIONS

Savoir et al, Triterpenes. XI. Presence of 11-keto-B-boswellic acid in Incense, 1967, bulletin des Brussels chimiques Belges, 76(5-6), 368-70, ( two pages of abstract ).*
International Search Report mailed on Mar. 18, 2005.

* cited by examiner

Primary Examiner—Taylor Victor Oh
(74) Attorney, Agent, or Firm—Rader, Fishman & Grauer, PLLC

(57) ABSTRACT

This invention relates to novel AKBA analogs of the formula I given below:

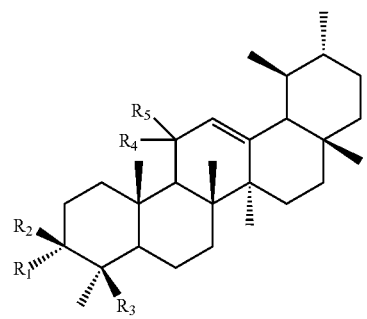

Where in $R_1$, $R_2$, $R_3$, $R_4$ and $R_5$ in each of the said analogs are:
1. $R_1$=OCHO, $R_2$=H, $R_3$=COOH, $R_4$ & $R_5$=O
2. $R_1$=OCOCH$_2$Cl, $R_2$=H, $R_3$=COOH, $R_4$ & $R_5$=O
3. $R_1$=5'-O-methylgalloyloxy, $R_2$=H, $R_3$=COOH, $R_4$ & $R_5$=O
4. $R_1$=OCOCH$_2$CH$_2$COOH, $R_2$=H, $R_3$=COOH, $R_4$ & $R_5$=O
5. $R_1$=8',9'-Dihydro-4'-hydroxycinnamoyloxy, $R_2$=H, $R_3$=COOH, $R_4$ & $R_5$=O
6. $R_1$=4'-Hydroxycinnamoyloxy, $R_2$=H, $R_3$=COOH, $R_4$ & $R_5$=O
7. $R_1$=3',4'-Dimethoxycinnamoyloxy, $R_2$=H, $R_3$=COOH, $R_4$ & $R_5$=O
8. $R_1$=3',4'-Dihydroxy-5'-methoxycinnamoyloxy, $R_2$=H, $R_3$=COOH, $R_4$ & $R_5$=O
9. $R_1$=OCOCH$_2$NH(tert-BOC), $R_2$=H, $R_3$=COOCH$_3$, $R_4$ & $R_5$=O
10. $R_1$=OCOCH$_2$NH$_2$HCl, $R_2$=H, $R_3$—COOH, $R_4$ & $R_5$=O
11. $R_1$=OCOCH(CH$_3$)NH$_2$HCl, $R_2$=H, $R_3$=COOH, $R_4$ & $R_5$=O
12. $R_1$=H, $R_2$=OH, $R_3$=COOCH$_3$, $R_4$ & $R_5$=O
13. $R_1$=H, $R_2$=Br, $R_3$ COOCH$_3$, $R_4$ & $R_5$=O
14. $R_1$=CN, $R_2$=H, $R_3$=COOCH$_3$, $R_4$ & $R_5$=O
15. $R_1$=SH, $R_2$=H, $R_3$=COOCH$_3$, $R_4$& $R_5$=O
16. $R_1$ & $R_2$=N(OH), $R_3$=COOCH$_3$, $R_4$ & $R_5$=O
17. $R_1$ & $R_2$=H & OCOCH$_3$ $R_3$=H, $R_4$ & $R_5$=O
18. $R_1$=OCOCH$_3$, $R_2$=H $R_3$=COOCH$_2$CH$_2$N(CH$_3$)$_2$, $R_4$ & $R_5$=O
19. $R_1$=OCOCH$_3$, $R_2$=H $R_3$=CONH$_2$, $R_4$ & $R_5$=O
20. $R_1$=OCOCH$_3$, $R_2$=H, $R_3$=CONHNH$_2$, $R_4$ & $R_5$=O
21. $R_1$=OCOCH$_3$, $R_2$=H, $R_3$=CONHCH$_2$CH$_2$NH$_2$, $R_4$ & $R_5$=O
22. $R_1$=OCOCH$_3$, $R_2$=H, $R_3$=CONHCH$_2$CH$_2$OH, $R_4$ & $R_5$=O
23. $R_1$=OCOCH$_3$, $R_2$=H, $R_3$=CON(CH$_2$CH$_2$)$_2$NH, $R_4$ & $R_5$=O
24. $R_1$=OCOCH$_3$, $R_2$=H $R_3$=NCO, $R_4$ & $R_5$=O
25. $R_1$=OCOCH$_3$, $R_2$=H $R_3$=NH$_2$, $R_4$ & $R_5$=O 26. $R_1$=OCOCH$_3$, $R_2$=H $R_3$=CN, $R_4$ & $R_5$=O
27. $R_1$=OH, $R_2$=H $R_3$=COOH, $R_4$ & $R_5$=OH & H These compounds exhibited 5-Lipoxigenase inhibitory properties and these compounds may be used in pharmaceutical compositions for therapeutic applications against a variety of inflammations and hypersensitivity-based human diseases including asthma, arthritis, bowel diseases such as ulcerative colitis and circulatory disorders such as shock and ischaemia. These compounds also inhibited the growth of Brine Shrimp in cultures, which may be considered as a positive indication for cytotoxicity and antitumor activity.

30 Claims, No Drawings

ANALOGS OF 3-O-ACETYL-11-KETO-β-BOSWELLIC ACID

This invention relates to novel structural analogs of 3-O-acetyl-11-keto-β-boswellic acid (AKBA).

TECHNICAL FIELD

Presently, there has been a tremendous surge in demand for non-steroidal, plant based antiiflammatory agents. 5-Lipoxygenase is the key enzyme for the biosynthesis of leukotrienes and 5(S)-HETE, the important mediators for inflammatory, allergic and obstructive process, from arachidonic acid. 5-Lipoxygenase is the target enzyme for identifying inhibitors, which have potential to cope with a variety of inflammations and hypersensitivity-based human diseases including asthma, arthritis, bowel diseases such as ulcerative colitis and circulatory disorders such as shock and ischaemia. Scientists around the world have invested a major effort during the last ten years, in identifying 5-lipoxygenase inhibitors.

Gum resin of *Boswellia* species known as Indian frankincense has been used as an anti-inflammatory agent in Traditional Ayurvedic Medicine in India. Ancient Ayurvedic texts described its therapeutic use. Clinical trails performed by CSIR laboratories in India have shown fair to excellent results in 88% of the patients, with no adverse side effects [Singh, G. B., *Status report, anti-inflammatory drugs from plant sources* (1982)]. A randomized, double blind, placebo controlled clinical trials on patients with Osteo-arthritis of knee exhibited statistically significant improvement in the pain, decreased swelling and increased knee flexion etc. [*Kimmatkar, Phytomedicine* 10: 3-7 (2003)]. The therapeutic effects shown by *Boswellia serrata* extract were comparable to those exhibited by sulfasalazine and mesalazine in patients with ulcerative colitis. (Gupta, I., et al., *Eur. J. Med. Res.,* 3: 511-14, 1998 and Gerhardt, H., et. al., *Gastroenterol.,* 39: 11-17, 2001). The source of anti-inflammatory actions has been attributed to boswellic acids (Safayhi, H., et al., *Planta Medica* 63, 487-493, 1997 and *J. Pharmacol. Exp. Ther.* 261, 1143-46, 1992, both the journals published from USA), a group of triterpene acids isolated from the *Boswellia* resin (Pardhy, R. S., et al., *Indian J. Chem.,* 16B, 176-178, 1978). These compounds exert anti-inflammatory activity by inhibiting 5-lipoxygenase (5-LO). Immunomodulatory activity of boswellic acids had been reported by Sharma et. al. in *Phytotheraphy Research*, (10, 107-112, 1996), published from USA. A detailed study on the structural requirements for boswellic acids indicated that, of all the six boswellic acids, 3-O-acetyl-11-keto-β-boswellic acid, hereinafter referenced as AKBA shows most pronounced inhibitory activity against 5-LO (Sailer, E. R., et al, *British J. Pharmacology,* 117, 615-618, 1996). AKBA acts by unique mechanism, in which it binds to 5-LO in a calcium-dependent and reversible manner and acts as a non-redox-type, non-competitive inhibitor (Sailer, E. R., et al., *Euro. J. Biochem.,* 256, 364-368, 1998). AKBA has thus become the subject of intensive research for its potential for the treatment of chronic inflammatory disorders.

The oleanane and ursane triterpenoids also gained prominence recently for their antiproliferative actions. As 5-lipoxygenase (5-LO) is the first enzyme in the metabolic pathway leading to the formation of leukotrienes and eicosanoids that are important in carcinogenesis process, inhibitors of 5-LO may thus have profound influence on the growth and apoptosis of various cancer lines (Yong S. Park, et. al. *Planta Medica,* 68, 397-401, 2002). Boswellic acids, for example inhibited several leukemia cell lines in vitro and inhibited melanoma growth and induced apoptosis (Hostanska, K., et al., *Anticancer Res.,* 22(5), 2853-62, 2002). The acetyl boswellic acids were found to be unique class of dual inhibitors of human topoisomerases I and II α (Syrovets, T. et al., *Mol. Pharmacol.,* 58 (1), 71-81, 2000). A number of oleanane and ursane triterpenoids were found to be powerful inhibitors of nitric oxide production in macrophases, which can be correlated to their cancer chemoprevention activity. (Honda, T., et. al., *J. Med. Chem.,* 43, 1866-1877).

BACKGROUND ART

5-Lipoxigenase inhibitory properties of AKBA and other boswellic acids have been scientifically established. Efforts are currently being made to enrich AKBA in the natural extracts and also to synthesize structural analogs of AKBA with enhanced potency and water solubility.

DISCLOSURE OF THE INVENTION

The organic solvent extract of the gum resin of *Boswellia serrata* contain a total of six boswellic acids. These acids are shown in FIG. 1, and are represented by B1, B2, B3, B4, B5 and B6. The concentration of most active principle B2 (AKBA) amounts only in the range of 1-10%, but most typically in the range of 2-3%. The enrichment of AKBA from natural *Boswellia* extract has already been undertaken by the inventors and described in international patent application (PCT # WO 03/074063, dtd. 12 Sep. 2003) and U.S. patent application (U.S. #2004073060). The potential usefulness of boswellic acids in general and AKBA in particular can be a great incentive to take-up further development of these compounds in all possible aspects. The present invention is related to development of novel structural analogs of AKBA by semi-synthesis from 11-keto-β-boswellic acid (KBA) or 3-O-acetyl-11-keto-β-boswellic acid (AKBA) for biological evaluation and to conduct structure activity relationship studies. The core objective of this invention is to obtain novel AKBA type compounds with enhanced biological activity and improved water solubility for use in therapeutic applications as anti-inflammatory, anti-arthritic and anti-tumor agents.

A systematic study on the boswellic acids analog development has not been undertaken, so far, except the preparation of some arylidene analogs of 3-keto-β-boswellic acid (Gupta, V. N. et. al., *Indian Drugs,* 25(2), 70-72, 1987). The major functional moieties that can be expended to make novel structural analogs of AKBA are acetoxyl, carboxyl and enone. Two major types of compounds were primarily envisioned for the development of new analogs of AKBA. One type constitutes a group, which differ in the nature of the acyloxy group on C3 of the ring A. The other group contains compounds obtained by modification of carboxyl group on C4 of the unit A.

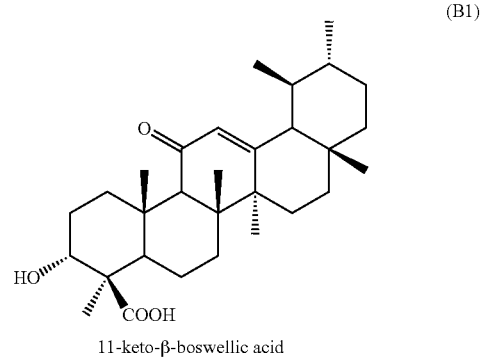

FIG. 1

11-keto-β-boswellic acid

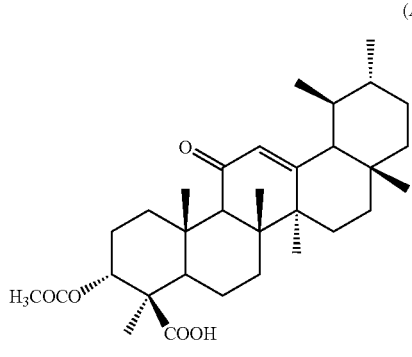

3-O-acetyl-11-keto-β-boswellic acid (AKBA, B2)

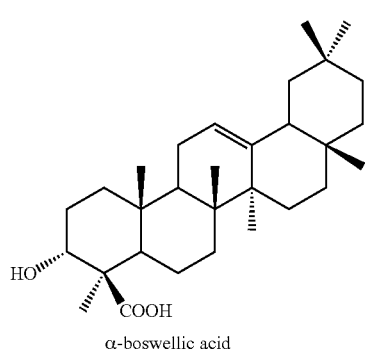

α-boswellic acid (B3)

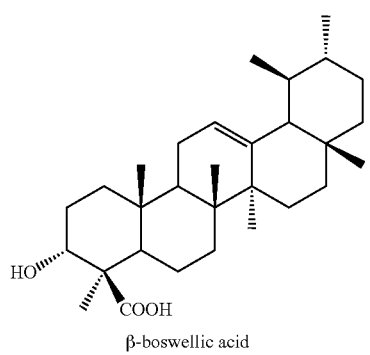

β-boswellic acid (B4)

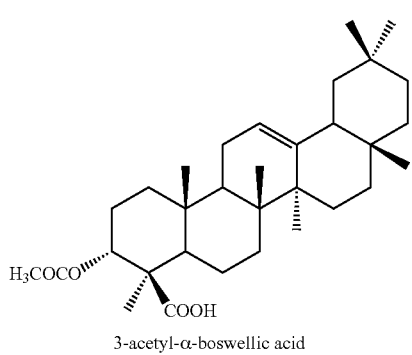

3-acetyl-α-boswellic acid (B5)

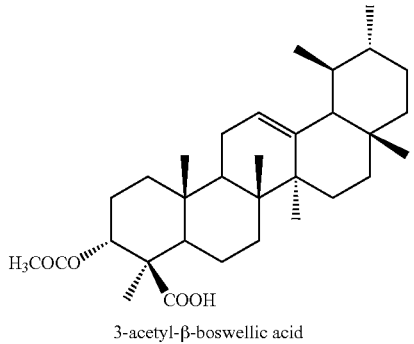

3-acetyl-β-boswellic acid (B6)

This invention relates to novel structural analogs of 3-O-acetyl-11-keto-β-boswellic acid (AKBA) having the formula.

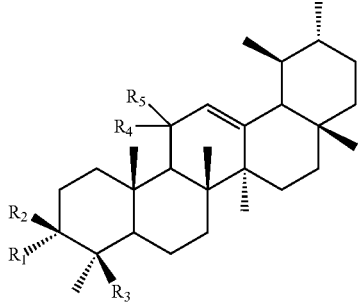

I

Where in $R_1$, $R_2$, $R_3$, $R_4$ and $R_5$ are as indicated below in each of said analogs:

1. $R_1$=OCHO, $R_2$=H, $R_3$=COOH, $R_4$ & $R_5$=O
2. $R_1$=OCOCH$_2$Cl, $R_2$=H, $R_3$=COOH, $R_4$ & $R_5$=O
3. $R_1$=5'-O-methylgalloyloxy, $R_2$=H, $R_3$=COOH, $R_4$ & $R_5$=O
4. $R_1$=OCOCH$_2$CH$_2$COOH, $R_2$=H, $R_3$=COOH, $R_4$ & $R_5$=O
5. $R_1$=8',9'-Dihydro-4'-hydroxycinnamoyloxy, $R_2$=H, $R_3$=COOH, $R_4$ & $R_5$=O
6. $R_1$=4'-Hydroxycinnamoyloxy, $R_2$=H, $R_3$=COOH, $R_4$ & $R_5$=O
7. $R_1$=3',4'-Dimethoxycinnamoyloxy, $R_2$=H, $R_3$=COOH, $R_4$ & $R_5$=O
8. $R_1$=3',4'-Dihydroxy-5'-methoxycinnamoyloxy, $R_2$=H, $R_3$=COOH, $R_4$ & $R_5$=O
9. $R_1$=OCOCH$_2$NH(tert-BOC), $R_2$=H, $R_3$=COOCH$_3$, $R_4$ & $R_5$=O
10. $R_1$=OCOCH$_2$NH$_2$HCl, $R_2$=H, $R_3$=COOH, $R_4$ & $R_5$=O
11. $R_1$=OCOCH(CH$_3$)NH$_2$HCl, $R_2$=H, $R_3$=COOH, $R_4$ & $R_5$=O
12. $R_1$=H, $R_2$=OH, $R_3$=COOCH$_3$, $R_4$ & $R_5$=O
13. $R_1$=H, $R_2$=Br, $R_3$=COOCH$_3$, $R_4$ & $R_5$=O
14. $R_1$=CN, $R_2$=H, $R_3$=COOCH$_3$, $R_4$ & $R_5$=O
15. $R_1$=SH, $R_2$=H, $R_3$=COOCH$_3$, $R_4$ & $R_5$=O
16. $R_1$ & $R_2$=N(OH), $R_3$=COOCH$_3$, $R_4$ & $R_5$=O
17. $R_1$ & $R_2$=H & OCOCH$_3$ $R_3$=H, $R_4$ & $R_5$=O
18. $R_1$=OCOCH$_3$, $R_2$=H $R_3$=COOCH$_2$CH$_2$N(CH$_3$)$_2$, $R_4$ & $R_5$=O
19. $R_1$=OCOCH$_3$, $R_2$=H $R_3$=CONH$_2$, $R_4$ & $R_5$=O 20. $R_1$=OCOCH$_3$, $R_2$=H, $R_3$=CONHNH$_2$, $R_4$ & $R_5$=O
21. $R_1$=OCOCH$_3$, $R_2$=H, $R_3$=CONHCH$_2$CH$_2$NH$_2$, $R_4$ & $R_5$=O
22. $R_1$=OCOCH$_3$, $R_2$=H, $R_3$=CONHCH$_2$CH$_2$OH, $R_4$ & $R_5$=O
23. $R_1$=OCOCH$_3$, $R_2$=H, $R_3$=CON(CH$_2$CH$_2$)$_2$NH, $R_4$ & $R_5$=O
24. $R_1$=OCOCH$_3$, $R_2$=H $R_3$=NCO, $R_4$ & $R_5$=O
25. $R_1$=OCOCH$_3$, $R_2$=H $R_3$=NH$_2$, $R_4$ & $R_5$=O
26. $R_1$=OCOCH$_3$, $R_2$=H $R_3$=CN, $R_4$ & $R_5$=O
27. $R_1$=OH, $R_2$=H $R_3$=COOH, $R_4$ & $R_5$=OH & H The structures of the individual compounds are presented below in FIG. 2.

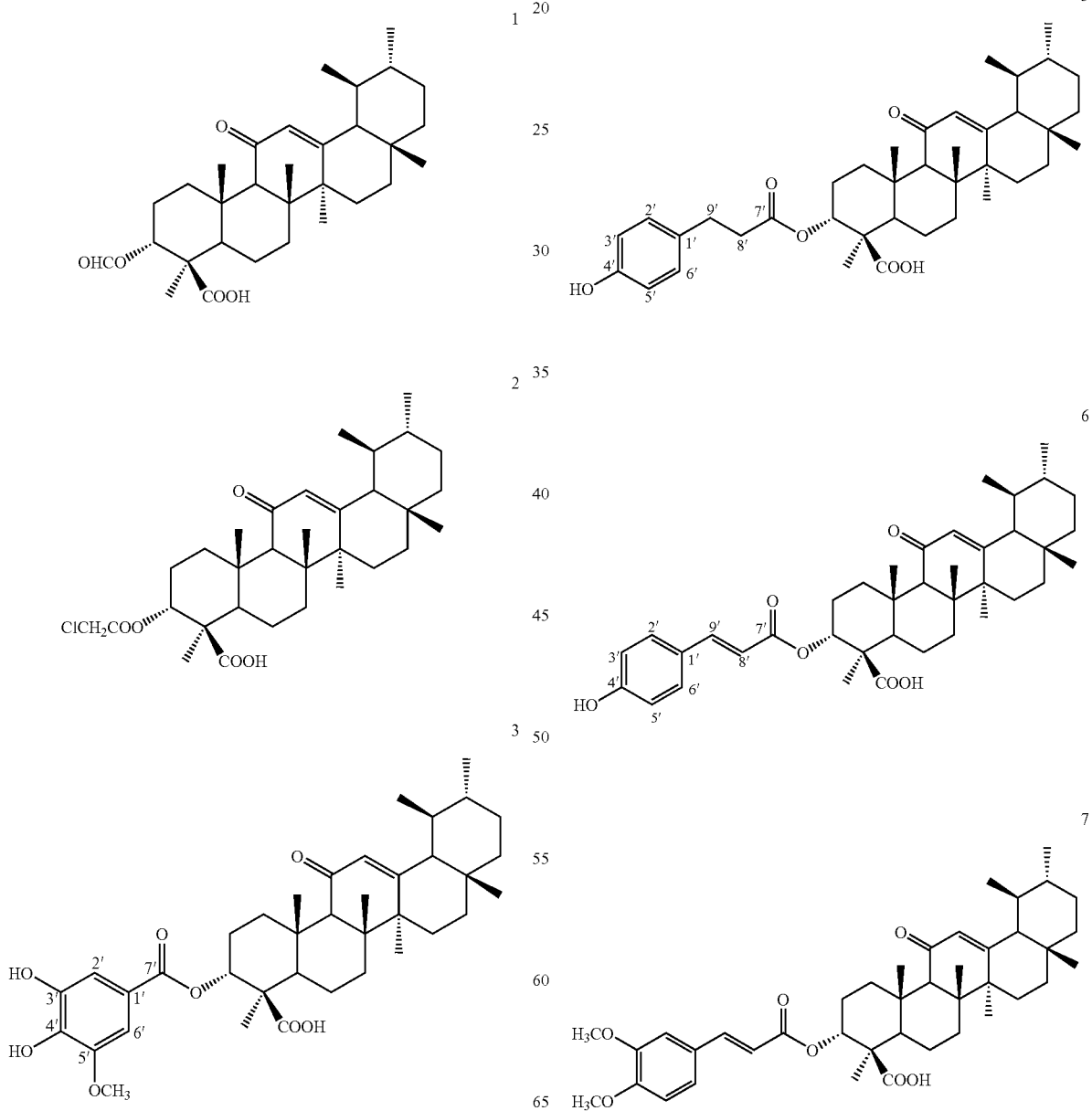

FIG. 2

-continued
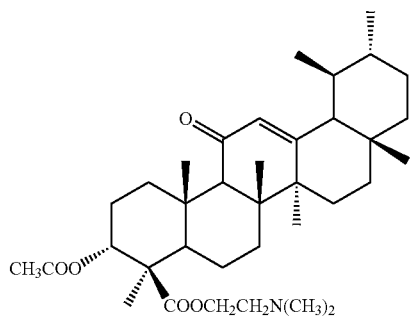
18
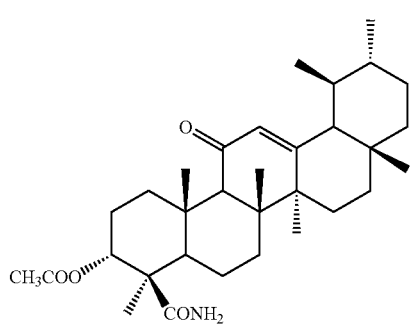
19
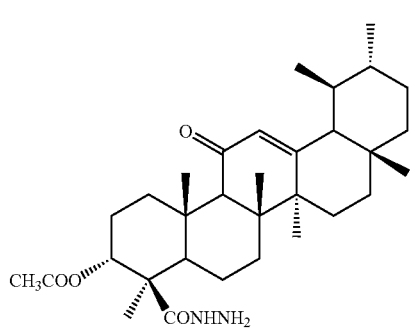
20
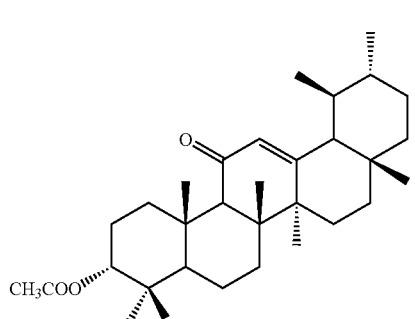
21
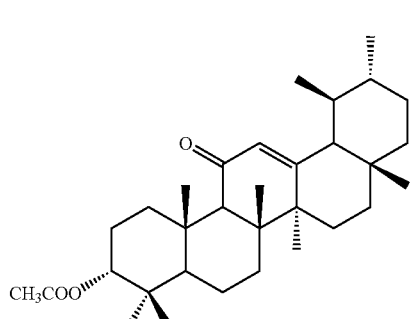
22
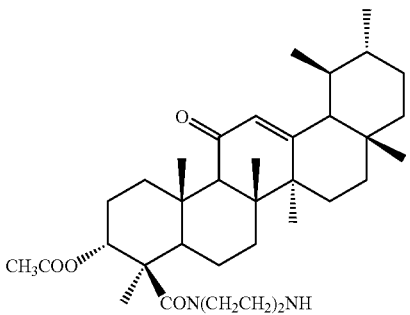
23
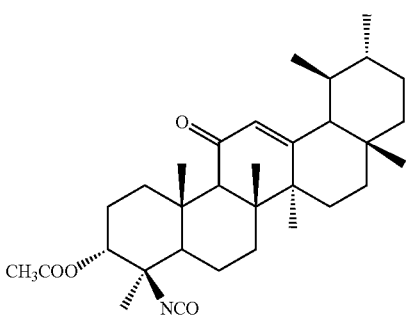
24
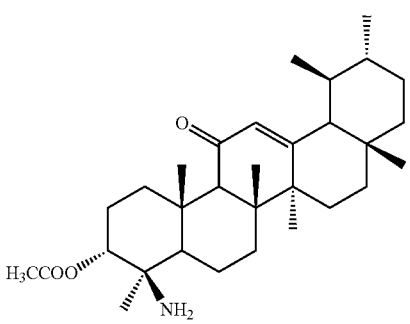
25
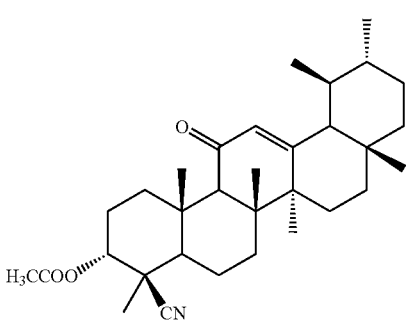
26
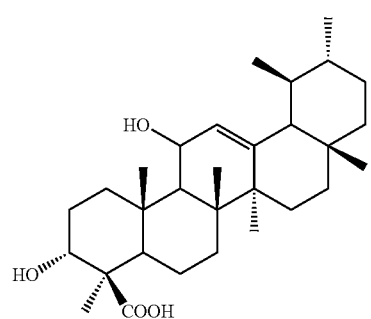
27

The preferred compounds of the invention are
1. 3-O-Formyl-11-keto-β-boswellic acid, 1
2. 3-O-(Chloroacetyl)-11-keto-β-boswellic acid, 2
3. 3-O-(5'-O-methylgalloyl)-11-keto-β-boswellic acid, 3
4. 3-O-Succinyl-11-keto-β-boswellic acid, 4
5. 3-O-[8',9'-Dihydro-4'-hydroxycinnamoyl]-11-keto-β-boswellic acid, 5
6. 3-O-[4'-Hydroxycinnamoyl]-11-keto-β-boswellic acid, 6
7. 3-O-(3',4'-dimethoxycinnamoyl)-11-keto β-boswellic acid, 7
8. 3-O-(3',4'-Dihydroxy-5'-methoxycinnamoyl)-11-keto-β-boswellic acid, 8
9. Methyl 3-O-(N-Boc-glycyl)-11-keto-β-boswellate, 9
10. 3-O-Glycyl-11-keto-β-boswellic acid hydrochloride, 10
11. 3-O-Alanyl-11-keto-β-boswellic acid hydrochloride, 11
12. Methyl 3β-hydroxy-11-ketours-12-en-24-oate, 12
13. Methyl 3β-bromo-11-ketours-12-en-24-oate, 13
14. Methyl 3α-cyano-11-ketours-12-en-24-oate, 14
15. Methyl 3α-thiohydroxy-11-ketours-12-en-24-oate, 15
16. Methyl 3-oximino-11-ketours-12-en-24-oate, 16
17. 3-Acetoxy-11-keto-24-norurs-12-ene, 17
18. (2'-N,N-Dimethylaminoethyl) 3-O-acetyl-11-keto-β-boswellate, 18
19. 3-O-Acetyl-11-keto-β-boswellic acid amide, 19
20. N-(3-O-Acetyl-11-keto-β-boswelloyl)-hydrazide, 20
21. N-(3-O-Acetyl-11-keto-β-boswelloyl)-ethylenediamine, 21
22. N-(3-O-Acetyl-11-keto-β-boswelloyl)-2-aminoethanol, 22
23. N-(3-O-Acetyl-11-keto-β-boswelloyl)-piperzine, 23
24. 3-Acetoxy-11-keto-24-norurs-12-en-4-isocyanate, 24
25. 3-Acetoxy-4-amino-11-keto-24-norurs-12-ene, 25
26. 3-Acetoxy-4-cyano-11-keto-24-norurs-12-ene, 26
27. 11-Hydroxy-β-boswellic acid, 27

Novel compounds of this invention may be prepared by the following processes.

The compounds represented by 2 to 11 may be prepared by a coupling reaction between KBA or its ester with an appropriate acid counterpart using DCC (1,3-dicyclohexylcarbodiimide) and DMAP {4-(dimethylamino)pyridine} as coupling agent in a suitable solvent system. This may also be accomplished by converting the acid corresponding to the acyloxy unit to the acid chloride using SOCl$_2$ (thionyl chloride) and then treating the acid chloride with KBA or its methyl ester, in the presence of an organic base. The compounds represented by 12, 13, 14 and 15 may be prepared by displacing the 3αOH group in methyl ester of KBA by Br using PBr$_3$ (phosphorus tribromide) and then further displacing the Br group with appropriate nucleophilic agents, such as SH⁻, CN⁻ etc. These reaction sequences are shown hereinafter in scheme I.

The amide compounds represented by 19, 20, 21, 22 and 23 may be prepared by treating the acid chloride of AKBA with an excess of amine component in a suitable solvent system. This reaction scheme is shown in the scheme II below.

The isocyanate and amine compounds represented by the structures 24 and 25 respectively may be prepared by Hoffmann rearrangement of the amide 19. The intermediate isocyanate, 24 may be obtained by reducing the reaction time and working-up the reaction before completion.

The isolation of starting materials AKBA and KBA for the semi-synthesis of the novel analogs is accomplished by the procedures known in the literatures (For example, U.S. patent application No. 2004073060). Preferred embodiments relating to the processes of preparing AKBA analogs mentioned in the foregoing discussion and other compounds of the subject invention are illustrated in the following examples, 1 to 27. These analogs inhibited 5-Lipoxigenase enzyme and also the growth of Brine Shrimp in cultures.

Scheme I

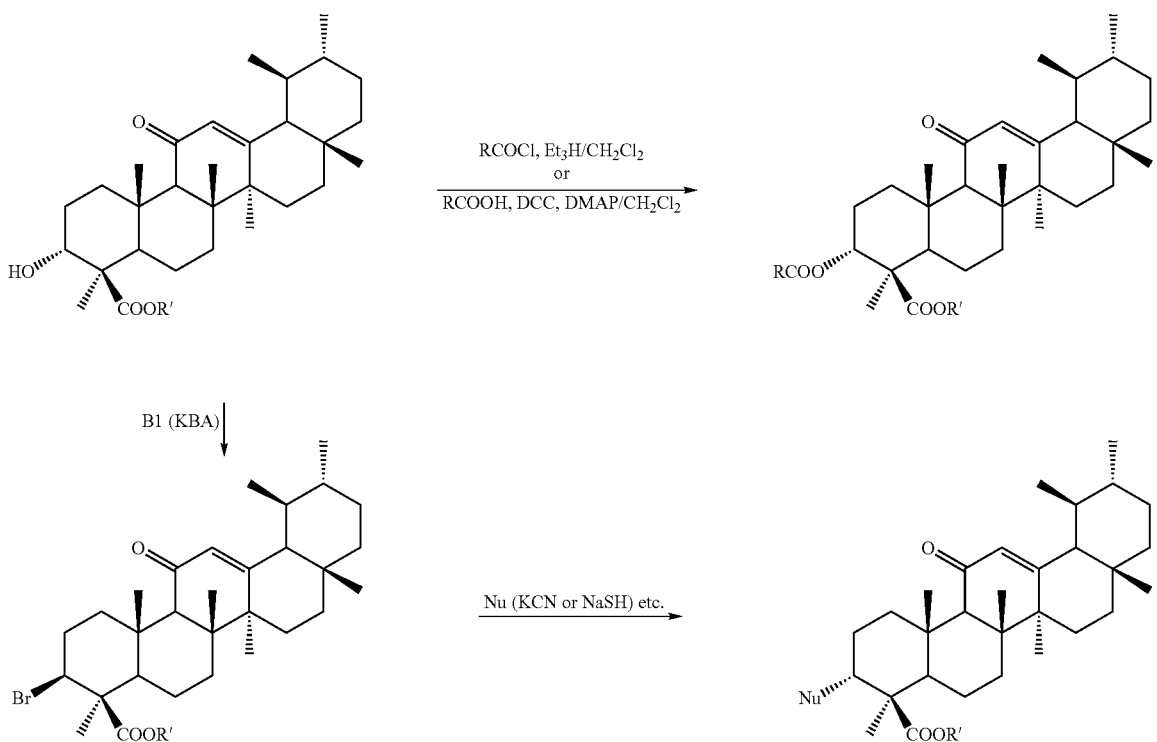

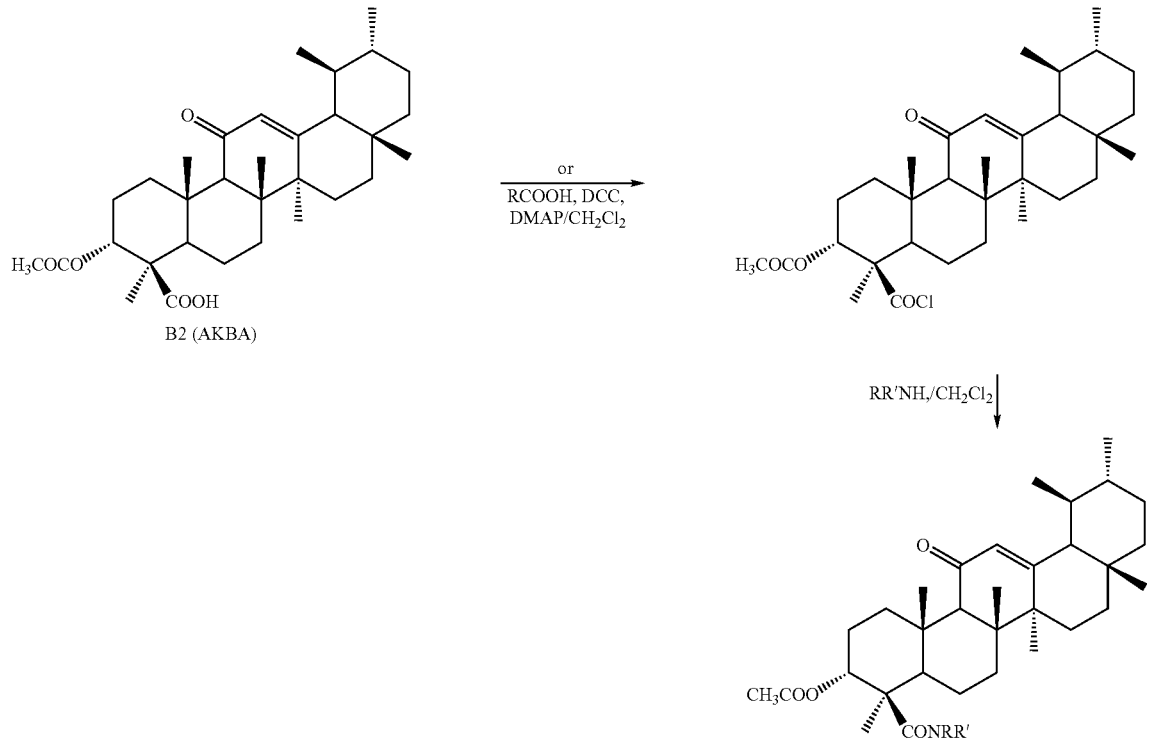

Scheme II

EXAMPLE 1

3-O-Formyl-11-keto-β-boswellic acid (1): To a solution of 11-keto-β-boswellic acid (200 mg, 0.424 mmol) in DMF (2 mL), cooled in an ice water bath was slowly added phosphorous oxychloride (150 μL, 1.7 mmol). The reaction mixture was allowed to warm-up to the ambient temperature and the stirring was continued. After 2 h, the reaction mixture was poured into ice water and extracted with ethyl acetate (2×25 mL). The combined organic extract was washed with brine, dried over $Na_2SO_4$ and evaporated under reduced pressure. The residue was subjected to silica column chromatography using hexane and ethyl acetate mixtures. The fractions eluted with 10% ethyl acetate/hexane were monitored and those containing 3-O-formyl-11-keto-β-boswellic acid were combined and evaporated to obtain pure compound (120 mg). Melting point: 298-302° C.; $^1$HNMR (CDCl$_3$, 90 MHz): δ 0.50-2.50 (m, CH, CH$_2$ and CH$_3$ signals), 5.43 (1H, br s, 3-H), 5.60 (1H, s, 12-H), 8.20 (1H, s, —OC$\underline{H}$O); FT-IR (neat): 3400-2700 (br), 2924, 2859, 1727, 1705, 1662, 1459, 1270, 1166 cm$^{-1}$. LC-MS (positive mode): m/z 499 (M+H)$^+$, 521 (M+Na)$^+$, 1019 (2M+Na)$^+$.

EXAMPLE 2

3-O-(Chloroacetyl)-11-keto-β-boswellic acid (2): To a solution of 11-keto-β-boswellic acid (200 mg, 0.43 mmol) in CH$_2$Cl$_2$ (3 mL) was added chloroacetic acid (166 mg, 1.7 mmol) and DMAP (26 mg, 0.21 mmol), and the mixture was cooled in ice water. A solution of 1.75 g of DCC in 2 mL of CH$_2$Cl$_2$ was slowly added to the reaction mixture and the stirring continued at the same temperature. After 2 h, the solid was filtered and the filtrate was poured into ice water. The mixture was extracted with ethyl acetate (2×25 mL). The combined organic layer was washed with 0.5 N HCl (30 mL), water (30 mL) and brine (30 mL). The solvent was evaporated and the residue (250 mg) was subjected to silica column chromatography using hexane and ethyl acetate mixtures. The fractions eluted with 10% ethyl acetate/hexane were combined and the solvent evaporated to yield 3-O-(chloroacetyl)-11-keto-β-boswellic acid (150 mg). Melting point: 126-132° C.; $^1$H NMR (CDCl$_3$): δ 0.81 (3H, d; J=6.5 Hz, —CH$_3$), 0.83 (3H, s, —CH$_3$), 0.95 (3H, s, —CH$_3$), 1.07 (3H, s, —CH$_3$), 1.25 (3H, s, —CH$_3$), 2.11 (1H, m), 2.33 (1H, br t; J=12.7 Hz), 2.42 (1H, s), 2.56 (1H, d; J=12.7 Hz), 4.09 (2H, s, —C$\underline{H}_2$Cl), 5.40 (1H, br s, 3-H), 5.56 (1H, s, 12-H); FT-IR (neat): 3400-2700 (br), 2927, 2865, 1735, 1708, 1658, 1457, 1286, 1198, 992 cm$^{-1}$. LC-MS (positive mode): m/z 547 (M+H)$^+$, 569 (M+Na)$^+$, 1115 (2M+Na)$^+$.

EXAMPLE 3

3-O-(5'-O-methylgalloyl)-11-keto-β-boswellic acid (3): A solution of 11-keto-β-boswellic acid, (0.5 g, 1.06 mmoles), tri-O-methylgallic acid, (367 mg, 1.6 mmol) and DMAP (60 mg) in 5 ml of dichloromethane was stirred at 0° C., while a solution of DCC (330 mg, 1.6 mmol) in CH$_2$Cl$_2$ (3 mL) was slowly added. The reaction mixture was stirred at 0° C. for 1 h, and at room temp for 30 min. The reaction mixture was filtered and the filtrate diluted with CH$_2$Cl$_2$ (40 ml) and poured in to ice-water. The mixture was acidified with 0.1 N HCl and the layers separated. The organic layer was washed with water and brine, and dried over Na$_2$SO$_4$ and evaporated. The residue ((830 mg) was purified on silica column using hexane/ethyl acetate mixtures. The gallate containing fractions, obtained on elution with 15% ethyl acetate/hexane were combined and evaporated to yield 3-O-(tri-O-methyl-galloyl)-11-keto β-boswellic acid (580 mg, 82%).

To a mixture of AlCl$_3$ (590 mg, 4.4 mmol) and ClCH$_2$CH$_2$Cl (5 mL), stirred at RT for 15 min was added dropwise during 20 min a ClCH$_2$CH$_2$Cl (2 mL) solution of 3-O-(3,4,5-tri-O-methylgalloyl)-11-keto β-boswellic acid (580 mg, 0.87 mmol). After 3 h, the reaction mixture was poured into ice water and extracted with ethyl acetate (2×30 mL). The combined organic layer was washed with saturated NaHCO$_3$, water and brine, and then evaporated to obtain a residue, 3-O-(3',5'-di-O-methylgalloyl)-11-keto β-boswellic acid (560 mg, 98%).

To a cooled mixture of 3-O-(3',5'-di-O-methylgalloyl)-11-keto β-boswellic acid (200 mg, 0.31 mmol) and AlCl$_3$ (200 mg, 1.5 mmol) in ClCH$_2$CH$_2$Cl (2.5 mL) was slowly added pyridine (0.25 mL, 3.1 mmol). The mixture was subjected to reflux for 3.5 h. The reaction mixture was poured into ice water, acidified with dilute HCl and extracted with ethyl acetate (2×15 mL). The combined organic layer was washed with brine, dried over Na$_2$SO$_4$ and evaporated. The residue was subjected to silica column chromatography using ethyl acetate/hexane mixtures. The fractions eluted with 20% and 25% ethyl acetate/hexane mixtures were evaporated to obtain 3-O-(5'-O-methylgalloyl)-11-keto β-boswellic acid (80 mg, 41%). Melting point: 128-136° C.; $^1$H NMR (CDCl$_3$): δ 0.81 (3H, d; J=6.3 Hz, —CH$_3$), 0.84 (3H, s, —CH$_3$), 0.95 (3H, s, —CH$_3$), 1.22 (3H, s, —CH$_3$), 1.23 (3H, s, —CH$_3$), 1.26 (3H, s, —CH$_3$), 1.37 (3H, s, —CH$_3$), 2.34 (1H, m), 2.49 (1H, s), 2.62 (1H, d; J=13.3 Hz), 3.93 (3H, s, 5'-OCH$_3$), 5.52 (1H, br s, 3-H), 5.57 (1H, s, 12-H), 7.25 (1H, d; J=1.5 Hz, 2'-H), 7.30 (1H, d; J=1.5 Hz, 6'-H); IR (CHCl$_3$): 3400 (br), 2926, 2861, 1714, 1653, 1614, 1516, 1459, 1348, 1217, 1099, 1023 cm$^{-1}$; LC-MS (negative mode) 635 (M−H)$^-$.

EXAMPLE 4

3-O-Succinyl-11-keto-β-boswellic Acid (4): A mixture of 11-keto-β-boswellic acid (0.2 gm, 0.43 mmol), succinic anhydride (0.262 gm, 2.62 mmol), DMAP (51 mg, 0.42 mmol) and pyridine (1 mL) was stirred under reflux for 40 h. The mixture was poured into 20 ml of cold water and acidified to pH 4 with dil HCl. The solution was extracted with ethyl acetate (3×40 ml) and the combined organic layer was washed with brine, dried over Na$_2$SO$_4$ and evaporated. The residue was purified on a silica column eluting with hexane and ethyl acetate mixtures. The fractions eluted with 20% ethyl acetate/hexane were combined and evaporated to obtain the 3-O-succinyl-11-keto-β-boswellic acid (170 mg, 71%). Melting point: 172-176° C.; $^1$H NMR (CD$_3$OD): δ 0.78 (3H, d; J=6.4 Hz, —CH$_3$), 0.80 (3H, s, —CH$_3$), 0.92 (3H, s, —CH$_3$), 1.12 (3H, s, —CH$_3$), 1.16 (3H, s, —CH$_3$), 1.17 (3H, s, —CH$_3$), 1.35 (3H, s, —CH$_3$), 2.45 (1H, s), 2.46 (1H, m), 2.56-2.67 (4H, m, —OCOCH$_2$CH$_2$COOH), 5.28 (1H, br s, 3-H), 5.50 (1H, s, 12-H). IR (KBr): 3600-2700 (br), 2926, 2855, 1735, 1708, 1656, 1456, 1417, 1385, 1202, 1164 cm$^{-1}$. LC-MS (positive mode) m/z 571 (M+H)$^+$, 593 (M+Na)$^+$, 609 (M+K)$^+$.

EXAMPLE 5

3-O-[8,9-Dihydro-4-hydroxycinnamoyl]-11-keto-β-boswellic acid (5)

3-O-(4'-Benzyloxycinnamoyl)-11-keto-β-boswellic acid

A mixture of 4-benzyloxycinnamic acid (250 mg) acid and thionyl chloride (0.2 ml) was reflux for 30 min. Excess thionyl chloride was removed and the residue was dried under high vacuum. The residue was dissolved in dry dichloromethane (2.5 ml) and added drop by drop to a mixture of 11-keto-β-boswellic acid (400 mg), triethyl amine (0.7 ml) and DMAP (20 mg) in dichlorimethane (5 ml). After 2 hours, the mixture was diluted with ether (60 ml) and washed with water (2×20 ml) and brine (20 mL), dried over Na$_2$SO$_4$ and evaporated. The residue was subjected to column chromatography over silica gel using hexane/ethyl acetate mixtures as eluants. The fractions eluted with 8-12% ethyl acetate/hexane were combined and evaporated to give 3-O-(4'-benzyloxycinnamoyl)-11-keto-β-boswellic acid (160 mg, 26%). $^1$H NMR (CDCl$_3$): δ 0.80 (3H, d; J=6.4 Hz, —CH$_3$), 0.82 (3H, s, —CH$_3$), 0.95 (3H, s, —CH$_3$), 1.16 (3H, s, —CH$_3$), 1.19 (3H, s, —CH$_3$), 1.31 (3H, s, —CH$_3$), 1.34 (3H, s, —CH$_3$), 2.25 (1H, br t; J=10.7 Hz), 2.42 (1H, s), 2.55 (1H, brd; 13.1 Hz), 5.11 (2H, br s, —OCH$_2$Ph), 5.32 (1H, brs, 3-H), 5.56 (1H, s, 12-H), 6.31 (1H, d; J=15.9 Hz, 8'-H), 6.99 (2H, d; J=8.8 Hz, 3'/5'-H), 7.50 (2H, d; J=8.8 Hz, 2'/6'-H), 7.73 (1H, d; J=15.9 Hz, 9'-H). IR (CHCl$_3$): 3431 (br), 2973, 2925, 2867, 1712, 1659, 1633, 1602, 1511, 1455, 1384, 1251, 1160, 999, 827, 734 cm$^{-1}$; LC-MS (positive mode) m/z 729 (M+Na)$^+$, 1435 (2M+Na)$^+$.

Deprotection:

To a solution of 3-O-(4'-benzyloxycinnamoyl)-11-keto-β-boswellic acid (100 mg) in 3 mL of ethanol in a 10 mL RB flask was added 10 mg of 10% palladium on carbon. The RB flask was flushed with H$_2$ and the mixture was stirred under a positive H$_2$ pressure using a balloon. After 24 h, the mixture was filtered over celite and the solvent evaporated. The residue was subjected to silica column chromatography using hexane/ethyl acetate mixtures. The fractions eluted with 10% ethyl acetate/hexane yielded 3-O-(8',9'-dihydro-4'-hydroxycinnamoyl)-11-keto-β-boswellic acid. Melting point: 168-171° C.; $^1$H NMR (CDCl$_3$): δ 0.82 (3H, s, —CH$_3$), 0.83 (3H, d; J=7.7 Hz, —CH$_3$), 0.95 (3H, s, —CH$_3$), 1.08 (3H, s, —CH$_3$), 1.10 (3H, s, —CH$_3$), 1.17 (3H, s, —CH$_3$), 1.34 (3H, s, —CH$_3$), 2.34 (1H, s), 2.43 (1H, brd; 13.1 Hz), 2.66-2.58 (2H, m, —OCOCH$_2$CH$_2$Ar), 2.84-2.96 (2H, m, —OCOCH$_2$CH$_2$Ar), 5.24 (1H, brs, 3-H), 5.56 (1H, s, 12-H), 6.73 (2H, d; J=8.2 Hz, 3'/5'-H), 7.05 (2H, d; J=8.2 Hz, 2'/6'-H); IR (CHCl$_3$): 3433 (br), 2925, 2856, 1730, 1714, 1645, 1516, 1455, 1382, 1266, 768 cm$^{-1}$; LC-MS (positive) m/z 619 (M+H)$^+$, 641 (M+Na)$^+$.

EXAMPLE 6

3-O-(4-Hydroxycinnamoyl)-11-keto-β-boswellic acid (6): A mixture of 3-O-(4'-benzyloxycinnamoyl)-11-keto-β-boswellic acid (100 mg, 0.14 mmol), N,N-dimethylaniline (50 μl) and AlCl$_3$ (50 mg, 0.42 mmol) in CH$_2$Cl$_2$ (2 mL) was stirred at room temperature for 48 h. The reaction mixture was poured into ice water, acidified with 2N HCl and extracted with ethyl acetate. The organic layer was washed with brine, dried over Na$_2$SO$_4$ and evaporated. The residue was purified over a silica column using ethyl acetate/hexane mixtures. The fractions eluted with 30% ethyl acetate/hexane mixture yielded 3-O-(4'-hydroxycinnamoyl)-11-keto-β-boswellic acid (15 mg) after evaporation. Melting point: 180-185° C.; IR (CHCl$_3$): 3429 (br), 2926, 2854, 1721, 1656, 1600, 1457, 1379, 1267, 1164 cm$^{-1}$; LC-MS (positive) m/z 617 (M+H)$^+$, 639 (M+Na)$^+$, 1255 (2M+Na)$^+$.

EXAMPLE 7

Preparation of 3-O-(3,4-dimethoxycinnamoyl)-11-keto O-boswellic acid (7)

A solution of 11-keto-β-boswellic acid, (500 mg, 1.06 mmoles), 3,4-dimethoxycinnamic acid, (332 mg, 1.59 mmol) in 4 ml of dichloromethane was stirred at 0° C., and treated slowly with DCC (495 mg, 2.39 mmol) in 3 mL of dichloromethane at 0° C. Then DMAP (60 mg) was added and the stirring continued at 15-20° C. for 2 h. The reaction mixture was filtered, the mother liquor diluted with CH$_2$Cl$_2$ (40 ml), washed water (30 mL) and brine (30 mL), and dried over Na$_2$SO$_4$ and evaporated. The residue (1.1 g) was purified on silica column using hexane/ethyl acetate mixtures. The cinnamate containing fractions, eluted with 25-30% ethyl acetate/hexane were combined and evaporated to obtain 3-O-(3',4'-dimethoxycinnamoyl)-11-keto-β-boswellic acid (650 mg, 91%). Melting point: 146-150° C.; $^1$H NMR (CDCl$_3$): δ 0.83 (3H, d; J=6.4 Hz, —CH$_3$), 0.86 (3H, s, —CH$_3$), 0.97 (3H, s, —CH$_3$), 1.22 (3H, s, —CH$_3$), 1.24 (3H, s, —CH$_3$), 1.28 (3H, s, —CH$_3$), 1.32 (3H, s, —CH$_3$), 2.34 (1H, m), 2.49 (1H, s), 2.62 (1H, brd; J=9.4 Hz), 3.94 (3H, s, 3' or 4'-OCH$_3$), 3.92 (3H, s, 4' or 3'-OCH$_3$), 5.49 (1H, brs, 3-H), 5.59 (1H, s, 12-H), 6.36 (1H, d; J=15.9 Hz, 8'-H), 6.89 (1H, d; J=8 Hz, 5'-H), 7.08 (1H, br s, 2'-H), 7.13 (1H, d; J=8.0 Hz, 6'), 7.66 (1H, brd; J=15.9 Hz, 9'-H); IR (CHCl$_3$): 3406(br), 2929, 2860, 1712, 1655, 1516, 1458, 1260, 1150, 1024 cm$^{-1}$; LC-MS (positive) m/z 661 (M+H)$^+$, 683 (M+Na)$^+$, 699 (M+K)$^+$, 1343 (2M+Na)$^+$.

EXAMPLE 8

3-O-(3,4-Dihydroxy-5-methoxycinnamoyl)-11-keto-β-boswellic acid (8): A mixture of 11-keto-β-boswellic acid (500 mg, 1.06 mmol), 3,4,5-trimethoxycinnamic acid (500 mg, 2.1 mmol), DMAP (65 mg, 0.53 mmol) in CH$_2$Cl$_2$ (6 mL) was cooled to 5° C. and treated slowly with a CH$_2$Cl$_2$ (4 mL) solution of DCC (438 mg, 2.13 mmol). After 2 h, the reaction mixture was filtered and the mother liquor was poured into crushed ice. The mixture was extracted with ethyl acetate (3×30 mL) and the combined organic layer was washed with 0.1 N HCl (40 mL), water (40 mL) and brine (40 mL), and dried over Na$_2$SO$_4$ The solvent was evaporated and the residue was subjected to silica column chromatography using hexane and ethyl acetate mixtures. The fractions eluted with 15% ethyl acetate/hexane yielded 3-O-(3',4',5'-trimethoxycinnamoyl)-11-keto-β-boswellic acid (810 mg).

AlCl$_3$ (262 mg, 1.97 mmol) was dispersed in ClCH$_2$Cl$_2$Cl (2 mL) and stirred at room temperature for 30 min. A solution of 3-O-(3',4',5'-trimethoxycinnamoyl)-11-keto-β-boswellic acid (170 mg) in ClCH$_2$Cl$_2$Cl (1.5 mL) was slowly added to the AlCl$_3$ solution, followed by pyridine (200 μL, 2.95 mmol) and the stirring continued at room temperature. After 2 h, the reaction mixture was poured into ice-water and the mixture acidified to pH 4 with dilute HCl and extracted with ethyl acetate (3×15 ml). The combined organic layer was washed with brine and dried over Na$_2$SO$_4$. The solvent was evaporated and the residue was subjected to silica column chromatography using hexane and ethyl acetate mixtures. The fractions eluted with 25% ethyl acetate/hexane yielded 3-O-(3', 4'-dihydroxy-5'-methoxycinnamoyl)-11-keto-β-boswellic acid (80 mg, 50%). Melting point: 178-181° C.; $^1$H NMR (CDCl$_3$): δ 0.81 (3H, d; J=6.4 Hz, —CH$_3$), 0.84 (3H, s, —CH$_3$), 0.95 (3H, s, —CH$_3$), 1.19 (3H, s, —CH$_3$), 1.22 (3H, s, —CH$_3$), 1.29 (3H, s, —CH$_3$), 1.40 (3H, s, —CH$_3$), 2.47 (1H, s), 2.59 (1H, brd; 13.4 Hz), 2.65 (1H, d; J=9.4 Hz), 3.92 (3H, s, 5'-OCH$_3$), 5.45 (1H, brs, 3-H), 5.57 (1H, s, 12-H), 6.32 (1H, d; J=15.8 Hz, 8'-H), 6.65 (1H, br s, 2'-H), 6.86 (1H, br s, 6'-H), 7.56 (1H, d; J=15.8 Hz, 9'-H). IR (CHCl$_3$): 3356 (br), 2925, 2855, 1711, 1633, 1603, 1516, 1459, 1381, 1278, 772 cm$^{-1}$. LC-MS (negative) m/z 661 (M–H)$^-$.

EXAMPLE 9

Methyl 3-O-(N-Boc-glycyl)-11-keto-β-boswellate (9): A mixture of 11-keto-β-boswellic acid methyl ester (130 mg, 0.27 mmol), N-(tert-butoxycarbonyl) glycine (61 mg, 0.34 m moles) and DCC (16 mg, 0.77 mmol) in dichloromethane (4 ml) was cooled to 0° C. To this solution was added DMAP (35 mg) and the stirring continued at 0° C. for 1 hour and at room temp for 48 h. The reaction mixture was filtered, diluted with diethyl ether (40 ml) and washed with 0.1 N HCl. The organic layer was washed with brine, dried over Na$_2$SO$_4$ and evaporated. The residue was purified on silica column using hexane and ethyl acetate mixtures as eluants. The fractions eluted with 14% ethyl acetate in hexane were evaporated to obtain methyl 3-O-(N-BOC-glycyl)-11-keto-β-boswellate (122 mg, 71%). Melting point: 126-130° C.; $^1$H NMR (CDCl$_3$): δ 0.80 (3H, d; J=6.4 Hz, —CH$_3$), 0.82 (3H, s, —CH$_3$), 0.95 (3H, s, —CH$_3$), 1.03 (3H, s, —CH$_3$), 1.17 (6H, s, 2×—CH$_3$), 1.34 (3H, s, —CH$_3$), 1.44 (9H, s, —C(CH$_3$)$_3$, 1.83-1.93 (1H, m), 2.05-2.15 (1H, m), 2.18-2.28 (1H, m), 2.40 (1H, s), 2.53 (1H, brd; 13.0 Hz), 3.68 (3H, s, —OCH$_3$), 3.94 (2H, s, 3-OCOCH$_2$NH(CO)OC(CH$_3$)$_3$, 5.04 (1H, br s, 3-OCOCH$_2$NH(CO)OC(CH$_3$)$_3$, 5.39 (1H, brs, 3-H), 5.54 (1H, s, 12-H). IR (KBr): 3419 (br), 2972, 2935, 2867, 1729(br), 1663, 1517, 1460, 1375, 1172 cm$^{-1}$ LC-MS (positive) m/z 664 (M+Na)$^+$, 680 (M+K)$^+$.

EXAMPLE 10

3-O-Glycyl-11-keto-β-boswellic acid hydrochloride (10): A mixture of 11-keto-β-boswellic acid (1 g, 2.12 mmol), BOC protected glycine (0.514 g, 3.19 mmol) and DMAP (120 mg) in dry CH$_2$Cl$_2$ (9 mL) at 0° C. was treated with DCC (0.68 g, 3.19 mmol) in CH$_2$Cl$_2$ (4 mL) under vigorous stirring. After 2 h, the reaction mixture was filtered and the filtrate was poured into ice water. The mixture was carefully neutralized with 0.1 N HCl and extracted with CH$_2$Cl$_2$ (2×60 mL). The combined organic layer was washed with brine (40 mL), dried over Na$_2$SO$_4$ and evaporated to obtain crude 3-O-(N-BOC-glycyl)-11-keto-β-boswellic acid (1.52 g). The residue was subjected silica column chromatography using 5-20% ethyl acetate/hexane mixtures as eluents. The fractions eluted with 15% and 20% ethyl acetate/hexane mixtures yielded pure 3-O-(N-BOC-glycyl)-11-keto-β-boswellic acid (1.3 g, 92%). $^1$H NMR (CDCl$_3$): δ0.81 (3H, d; J=6.4 Hz, —CH$_3$), 0.82 (3H, s, —CH$_3$), 0.95 (3H, s, —CH$_3$), 1.15 (3H, s, —CH$_3$), 1.19 (3H, s, —CH$_3$), 1.23 (3H, s, —CH$_3$), 1.34 (3H, s, —CH$_3$), 1.44 (9H, s, —C(CH$_3$)$_3$, 2.21-2.33 (1H, m), 2.40 (1H, s), 2.55 (1H, brd; 12.6 Hz), 3.94 (2H, s, 3-OCOCH$_2$NH(CO)OC(CH$_3$)$_3$, 5.06 (1H, br s, 3-OCOCH$_2$NH(CO)OC(CH$_3$)$_3$), 5.37 (1H, brs, 3-H), 5.55 (1H, s, 12-H).

A solution of 3-O-(N-BOC-glycyl)-11-keto-β-boswellic acid (300 mg) in 1 mL of CH$_2$Cl$_2$ cooled to 0° C. was treated slowly with 1.5 mL of 2.5 N HCl in dioxane. After 30 min, the stirring was continued over night at room temperature. The reaction mixture was evaporated under vacuum and re-dissolved in 0.2 mL CH$_2$Cl$_2$ and diluted with hexane (1 mL). A white solid was precipitated. It was filtered, washed with hexane and dried to afford a white powder (219 mg). It was further purified over silica column using $CH_2Cl_2$ and $CH_3OH/CH_2Cl_2$ mixtures. The fractions eluted with 10% $CH_3OH/CH_2Cl_2$ yielded 3-O-glycyl-11-keto-β-boswellic acid hydrochloride (150 mg). Melting point: 210-212° C.; $^1H$ NMR ($CD_3OD$): δ 0.82 (3H, d; J=6.4 Hz, —$CH_3$), 0.86 (3H, s, —$CH_3$), 0.97 (3H, s, —$CH_3$), 1.17 (3H, s, —$CH_3$), 1.21 (3H, s, —$CH_3$), 1.28 (3H, s, —$CH_3$), 1.37 (3H, s, —$CH_3$), 2.13-2.23 (1H, m), 2.27-2.38 (1H, m), 2.49 (1H, s), 2.56 (1H, brd; 13.4 Hz), 3.82 (2H, s, 3-OCOC$\underline{H}_2$$NH_2$HCl), 5.42 (1H, brs, 3-H), 5.52 (1H, s, 12-H); IR (KBr): 3500-2400, 2979, 2928, 2868, 1721 (br), 1660, 1512, 1456, 1387, 1165, 1053 $cm^{-1}$. LC-MS (positive ion mode): m/z 528 [(M−Cl)$^+$], 550 (M−HCl+Na)$^+$.

EXAMPLE 11

3-O-Alanyl-11-keto-β-boswellic acid hydrochloride (11): A mixture of 11-keto-β-boswellic acid (500 mg, 1.06 mmol), BOC protected alanine (320 mg, 1.69 mmol) and DMAP (75 mg) in dry $CH_2Cl_2$ (5 mL) at 0° C. in a 25 mL RB flask was treated with DCC (330 mg, 1.60 mmol) in $CH_2Cl_2$ (2 mL) under vigorous stirring. After 30 min, the stirring was continued at room temperature for 2 h. The reaction mixture was filtered and the filtrate was poured into ice water. The mixture was carefully acidified to pH 5 with 0.1 N HCl, and extracted with $CH_2Cl_2$ (2×60 mL). The combined organic layer was washed with brine, dried over $Na_2SO_4$ and evaporated to obtain 3-O-(N-BOC-alanyl)-11-keto-β-boswellic acid. The residue (550 mg) was subjected silica column chromatography using 5-20% ethyl acetate/hexane mixtures as eluents. The fractions eluted with 20% ethyl acetate/hexane mixture yielded 320 mg of pure 3-O-(N-BOC-alanyl)-11-keto-β-boswellic acid. $^1H$ NMR ($CDCl_3$): δ 0.81 (3H, d; J=6.4 Hz, —$CH_3$), 0.83 (3H, s, —$CH_3$), 0.95 (3H, s, —$CH_3$), 1.16 (3H, s, —$CH_3$), 1.20 (3H, s, —$CH_3$), 1.25 (3H, s, —$CH_3$), 1.34 (3H, s, —$CH_3$), 1.39 (3H, d; J=7.1 Hz, 3-OCOCH(C$\underline{H}_3$)NH(CO)OC($CH_3$)$_3$), 1.43 (9H, s, —OC(C$\underline{H}_3$)$_3$, 2.21-2.33 (1H, m), 2.40 (1H, s), 2.58 (1H, brd; 12.2 Hz), 4.27-4.42 (1H, s, 3-OCOC$\underline{H}$($CH_3$)NH(CO)OC($CH_3$)$_3$), 5.08 (1H, br s, 3-OCOCH($CH_3$)N$\underline{H}$(CO)OC($CH_3$)$_3$), 5.36 (1H, brs, 3-H), 5.56 (1H, s, 12-H); LC-MS (positive mode): m/z 655 (M+Na)$^+$.

A solution of 3-O-(N-BOC-alanyl)-11-keto-β-boswellic acid (200 mg) in 1 mL of $CH_2Cl_2$ cooled to 0° C. was treated slowly with 2.5 mL of 1 N HCl in dioxane. After 30 min, the stirring was continued over night at room temperature. The reaction mixture was concentrated and subjected to column chromatography over silica gel using $CH_2Cl_2$ and $CH_3OH/CH_2Cl_2$ mixtures. The fractions eluted with 10% $CH_3OH/CH_2Cl_2$ mixture afforded a white powder (90 mg) of 3-O-alanyl-11-keto-β-boswellic acid hydrochloride. Melting point: 212-214° C.; $^1H$ NMR ($CD_3OD$): δ 0.83 (3H, d; J=6.2 Hz, —$CH_3$), 0.86 (3H, s, —$CH_3$), 0.97 (3H, s, —$CH_3$), 1.17 (3H, s, —$CH_3$), 1.22 (3H, s, —$CH_3$), 1.25 (3H, s, —$CH_3$), 1.38 (3H, s, —$CH_3$), 1.58 (3H, d; J=6.8 Hz, 3-OCOCH(C$\underline{H}_3$)$NH_2$HCl), 2.15-2.23 (1H, m), 2.28-2.38 (1H, m), 2.50 (1H, s), 2.56 (1H, brd; 13.4 Hz), 4.15-4.23 (1H, s, 3-OCOC$\underline{H}$($CH_3$)$NH_2$HCl), 5.39 (1H, brs, 3-H), 5.53 (1H, s, 12-H); IR (KBr): 3500-2600, 2980, 2928, 2870, 1725, 1710, 1663, 1515, 1452, 1390, 1161, 1051 $cm^{-1}$. LC-MS (positive ion mode): m/z 542 (M−Cl)$^+$, 564 (M−HCl+Na)$^+$.

EXAMPLE 12

Methyl 3β-hydroxy-11-ketours-12-en-24-oate (12): Methyl 3,11-dioxours-12-en-24-oate (100 mg) was dissolved in methanol (2 mL), cooled to 0° C. and the solution was treated with $NaBH_4$ (15 mg). After 1 h, the reaction mixture was poured into ice water and extracted with ethyl acetate (2×20 mL). The combined extracts were washed with brine, dried over $NaSO_4$ and evaporated. The residue was purified over silica using ethyl acetate/hexane mixtures. The fractions eluted with 5% ethyl acetate/hexane were monitored and those containing the compound were combined and evaporated to obtain methyl 3β-hydroxy-11-ketours-12-en-24-oate (50 mg). Melting point: 250-254° C.; $^1$HNMR ($CDCl_3$): δ 0.80 (3H, d; J=6.4 Hz, —$CH_3$), 0.82 (3H, s, —$CH_3$), 0.95 (3H, d; J=7.1 Hz, —$CH_3$), 1.04 (3H, s, —$CH_3$), 1.17 (3H, s, —$CH_3$), 1.30 (3H, s, —$CH_3$), 1.42 (3H, s, —$CH_3$), 2.04-2.14 (1H, m), 2.32 (1H, s), 2.78 (1H, dt; J=13.5 and 3.6), 3.09 (1H, td; J=12.0 and 4.5 Hz), 3.29 (1H, d; J=12.0 Hz, 3-H), 3.69 (3H, s, —$OCH_3$), 5.55 (1H, s, 12-H); IR (KBr): 3400, 2924, 2859 1705, 1662, 1617, 1459, 1382, 1249, 1193, 991 $cm^{-1}$; LC-MS (positive mode) m/z 485 (M+H)$^+$, 507 (M+Na)$^+$, 991 (2M+Na)$^+$.

EXAMPLE 13

Methyl 30β-bromo-11-ketours-12-en-24-oate (13): A mixture of methyl 11-keto-β-boswellate (2 g, 4.13 mmol) and pyridine (85 μL, 1.03 mmol) in THF (18 mL) was cooled to −5° C. in ice-salt bath and treated slowly with $PBr_3$ (140 μL, 1.51 mmol) in THF (1 mL). After 2 h, $CH_3COOH$ (0.5 mL) was added and the stirring continued for another 15 min. The reaction mixture was poured into 5% ice-cold solution of $NaHCO_3$ (40 mL) and extracted with ethyl ether (4×40 mL). The combined organic layer was washed with brine, dried over $Na_2SO_4$ and evaporated. The residue was subjected to silica column chromatography using ethyl acetate/hexane mixtures. The fractions eluted with 15% ethyl acetate/hexane mixture were combined and evaporated to yield methyl 3β-bromo-11-ketours-12-en-24-oate (1.6 g, 75%). Melting point: 196-202° C.; $^1$HNMR ($CDCl_3$): δ 0.81 (3H, d; J=6.5 Hz, —$CH_3$), 0.82 (3H, s, —$CH_3$), 0.95 (3H, s, —$CH_3$), 1.03 (3H, s, —$CH_3$), 1.17 (3H, s, —$CH_3$), 1.31 (6H, s, 2×—$CH_3$), 2.28 (1H, br t; J=13.5), 2.39 (1H, d; J=4.2), 2.56 (1H, d; J=13.6 Hz), 3.66 (3H, s, —$CH_3$), 4.87 (1H, dd; J=17.7 and 10.1 Hz, 3-H), 5.54 (1H, s, 12-H); IR (KBr): 2977, 2926, 2867, 1722, 1660, 1617, 1456, 1384, 1262, 1201, 966, 756 $cm^{-1}$; LC-MS (positive mode): m/z 549 (M+H)$^+$, 571 (M+Na)$^+$, 587 (M+K)$^+$.

EXAMPLE 14

Methyl 3α-cyano-11-ketours-12-en-24-oate (14): A mixture of methyl 3β-bromo-11-ketours-12-en-24-oate (200 mg, 0.37 mmol), KI (18 mg, 0.11 mmol) and NaCN (35 mg, 0.71 mmol) in acetone (2 mL) was subjected to reflux for 2 h. The reaction mixture was poured into ice cold water and extracted with ethyl acetate (2×20 mL). The combined organic layer was washed with water (30 mL), brine (30 mL) and dried over $Na_2SO_4$. The solvent was evaporated and the residue was purified on silica column using hexane and ethyl acetate mixtures. The fractions eluted with 20% ethyl acetate/hexane were combined and evaporated to yield methyl 3α-cyano-11-ketours-12-en-24-oate (170 mg, 94%). Melting point: 150-152° C.; $^1$HNMR ($CDCl_3$): δ 0.81 (3H, d; J=6.5 Hz, —$CH_3$), 0.82 (3H, s, —$CH_3$), 0.95 (3H, d; J=7.1 Hz, —$CH_3$), 1.03 (3H, s, —$CH_3$), 1.17 (3H, s, —$CH_3$), 1.25 (3H, s, —$CH_3$), 1.26 (3H, s, —$CH_3$), 2.34/2.37 (1H, s), 2.54 (1H, br m), 3.63/3.67 (3H, s, —$OCH_3$), 4.91 (1H, dd; J=14.7 and 7.7 Hz, 3-H), 5.53/5.54 (1H, s, 12-H); IR (KBr): 3433 (br), 2978, 2925, 2859, 1724, 1664, 1459, 1383, 1235, 1197, 980 $cm^{-1}$; LC-MS (positive mode): m/z 493 (M+H)$^+$.

EXAMPLE 15

Methyl 3α-thiohydroxy-11-ketours-12-en-24-oate (15): To a solution of KSH, obtained by bubbling $H_2S$ through an ethanolic solution of KOH (350 mg in 10 mL), was added methyl 3β-bromo-11-ketours-12-en-24-oate (500 mg, 0.94 mmol) in 2 mL ethanol. The reaction mixture was stirred at room temperature for 16 h. The mixture was poured into ice-water and acidified with 2 N HCl and extracted with ethyl acetate (3×30 mL). The combined organic layer were washed with brine, dried over $Na_2SO_4$ and evaporated. The residue was subjected to column chromatography over silica gel using hexane and ethyl acetate mixtures. The fractions eluted with 25% and 30% ethyl acetate/hexane mixtures were evaporated to obtain methyl 3α-thiohydroxy-11-ketours-12-en-24-oate (180 mg, 39%). Melting point: 226-230° C.; $^1H$ NMR ($CDCl_3$): δ 0.80 (3H, d; J=6.5 Hz, —$CH_3$), 0.82 (3H, s, —$CH_3$), 0.95 (3H, s, —$CH_3$), 1.01 (3H, s, —$CH_3$), 1.15 (3H, s, —$CH_3$), 1.26 (3H, s, —$CH_3$), 1.34 (3H, s, —$CH_3$), 3.66 (3H, s, —$CH_3$), 4.76 (1H, t; J=13.2 Hz, 3-H), 5.51 (1H, s, 12-H); IR (KBr): 3430 (br), 2979, 2925, 2867, 1725, 1662, 1458, 1383, 1237, 1118, 975 $cm^{-1}$.

EXAMPLE 16

Methyl 3-oximino-11-ketours-12-en-24-oate (16): Nitrosomethyl urea (435 mg, 4.2 mmoles) was dissolved in ether (10 ml) and treated with aqueous potassium hydroxide (10%, 10 ml) at 5-10° C. for 15 min. The yellow coloured diazomethane layer was distilled and collected into a cooled diethyl ether (5 mL) solution of 11-keto-β-boswellic acid (415 mg, 0.88 mmoles). The stirring was continued at 5-10° C. for another 15 min. The solvent was evaporated and the residue was purified on a silica column using 4% EtOAc in hexane as eluant to obtain methyl 11-keto-β-boswellate (250 mg, 58.5%).

Oxidation

Method I: Methyl 11-ketoboswellate (205 mg, 0.423 mmoles) was dissolved in 5 ml of acetone and treated drop by drop with Jones reagent until the red colour of the reagent persists. The excess reagent was quenched by the addition of few drops of isopropanol. The reaction mixture was diluted with water (30 ml) and extracted with ether (2×50 ml). The organic layer was washed with brine and dried over $Na_2SO_4$ and evaporated to obtain methyl 3,11-diketours-12-en-24-oate (190 mg, 93.1%). IR ($CHCl_3$): 2975, 2950, 2919, 2874, 1719, 1651, 1457, 1388, 1327, 1234, 1197, 1096, 989 $cm^{-1}$; LC-MS (positive mode) m/z 482 $(M+H)^+$, 504 $(M+Na)^+$, 985 $(2M+Na)^+$.

Method II: To a solution of methyl 11-ketoboswellate (1 g, 2.07 mmol) in $CH_2Cl_2$ (35 mL) was added Jones reagent (3 mole equivalents) adsorbed on silica gel (6 g). The heterogeneous mixture was stirred at room temperature for 12 h. The reaction mixture was filtered to remove the reagent and the solvent evaporated. The residue was subjected to silica column chromatography using hexane and ethyl acetate mixtures. The fractions eluted with 5% ethyl acetate/hexane yielded methyl 3,11-diketours-12-en-24-oate (750 mg).

A solution of methyl 3,11-diketours-12-en-24-oate (150 mg, 0.31 mmol) in ethanol (5 ml) was added hydroxylamine hydrochloride, (110 mg, 1.5 mmol) and pyridine (0.25 ml). The mixture was refluxed at 80-90° C. After 1 hour, the mixture was poured into 5 ml of cold water. The white precipitate was filtered, washed thoroughly with distilled water and dried under high vacuum to obtain the methyl 3-oximino-11-ketours-12-en-24-oate (130 mg, 84.4%) as white solid.

Melting point: 238-240° C.; $^1H$ NMR ($CDCl_3$): δ 0.78 (3H, d; J=6.3 Hz, —$CH_3$), 0.82 (3H, s, —$CH_3$), 0.94 (3H, s, —$CH_3$), 1.17 (3H, s, —$CH_3$), 1.19 (3H, s, —$CH_3$), 1.26 (3H, s, —$CH_3$), 1.45 (3H, s, —$CH_3$), 2.03-2.13 (1H, m), 2.23-2.33 (1H, m), 2.34 (1H, s), 2.84-2.92 (1H, m), 3.25-3.33 (1H, m), 3.67 (3H, s, 24-COO$CH_3$), 5.56 (1H, s, 12-H), 7.58 (1H, br s, =NO$\underline{H}$); IR ($CHCl_3$): 3435, 2979, 2923, 2862, 1732, 1644, 1457, 1386, 1262, 1230, 941 $cm^{-1}$; LC-MS (positive mode) m/z 498 $(M+H)^+$, 520 $(M+Na)^+$, 1017 $(2M+Na)^+$.

EXAMPLE 17

3-Acetoxy-11-keto-24-norurs-12-ene (17): A mixture of methyl 3,11-diketours-12-en-24-oate (500 mg), lithium bromide (0.35 g) and pyridine (0.4 mL) in N,N-dimethylformamide (7 mL) was subjected to reflux over an oil bath on a magnetic stirrer. After six hours, the mixture was poured into ice-water and extracted with ethyl acetate. The organic layer was washed with 2N HCl followed by water and brine, and dried over $Na_2SO_4$. The solvent was evaporated and the residue (910 mg) was subjected to silica flash chromatography using hexane and ethyl acetate mixtures. The fractions eluted with 5% ethyl acetate/hexane were monitored by TLC and those containing the pure compound were combined and evaporated to obtain 3,11-diketo-24-norurs-12-ene as a semi solid. $^1H$ NMR ($CDCl_3$): δ 0.64 (1H, m), 0.80 (3H, d; J=6.5 Hz, —$CH_3$), 0.82 (3H, s, —$CH_3$), 0.94 (3H, s, —$CH_3$), 0.99 (3H, d; 6.3 Hz, —$CH_3$), 1.14 (3H, s, —$CH_3$), 1.17 (3H, s, —$CH_3$), 1.30 (3H, s, —$CH_3$), 1.89 (1H, dt; 13.6 and 4.8 Hz), 2.09 (1H, dt; 13.5 and 4.8), 2.35 (1H, s), 2.68 (1H, dt; 13.3 and 3.5), 3.09 (1H, dt; 10.1 and 5.99 Hz), 5.55 (1H, s, 12-H); IR ($CHCl_3$): 2926, 2870, 1710, 1662, 1615, 1457, 1384, 1200, 997 $cm^{-1}$; LC-MS (positive mode) m/z 425 $(M+H)^+$, 447 $(M+Na)^+$, 871 $(2M+Na)^+$.

The 3,11-diketo-24-norurs-12-ene (230 mg) was dissolved in methanol (5 mL) and treated with $NaBH_4$ (27 mg). After 30 min, the reaction mixture was poured into ice water and extracted with ethyl acetate (2×30 mL). The combined extracts were washed with brine, dried over $Na_2SO_4$ and evaporated. The residue was subjected to column chromatography over silica gel using hexane/ethyl acetate mixtures. The fractions eluted with 10% ethyl acetate/hexane were combined and evaporated to obtain 3-hydroxy-11-keto-24-norurs-12-ene (50 mg). It was dissolved in pyridine (0.1 mL) and treated with acetic anhydride (0.1 mL) at room temperature. After 3 h, the mixture was poured into ice water (10 mL) and extracted with ethyl acetate (20 mL). The organic layer was washed with brine, dried over $Na_2SO_4$ and evaporated to obtain 3-Acetoxy-11-keto-24-norurs-12-ene. IR ($CHCl_3$): 2924, 2859, 1732, 1654, 1454, 1379, 1262, 1242, 975, 885 $cm^{-1}$; LC-MS (positive mode) m/z 469 $(M+H)^+$, 491 $(M+Na)^+$, 959 $(2M+Na)^+$.

EXAMPLE 18

Preparation of (2-N,N-dimethylaminoethyl) 3-O-acetyl-11-keto-β-boswellate (18): A suspension of 2-N,N-dimethylaminoethylchloride (126 mg, 0.87 mmol), 3-O-acetyl-11-keto-β-boswellic acid (300 mg, 0.58 mmoles) and sodium carbonate (124 mg, 0.897 mmol) in acetone (5 ml) was stirred under refluxed at 60° C. After 2 h, the mixture was diluted with ether (30 mL) and filtered. The ether solution was washed with brine, dried over $Na_2SO_4$ and evaporated. The residue was purified on a silica column using hexane/EtOAc and ethylacetate/methanol mixtures. The fraction eluted with 10% methanol in ethyl acetate gave 2'-N,N-dimethylaminoethyl 3-O-acetyl-11-keto-β-boswellate (153 mg, 45%). Melt-

EXAMPLE 19

3-O-Acetyl-11-keto-β-boswellic acid amide (19): A mixture of 3-O-acetyl-11-keto-β-boswellic acid (300 mg) and thionyl chloride (0.5 mL) was refluxed for 1 h and the excess reagent was removed under reduced pressure to give the corresponding acid chloride. This crude acid chloride was dissolved in THF (1.0 mL) and treated drop-wise with conc. ammonia solution (3.0 mL) at ice-cold temp. for 5 min. and the mixture was stirred at the same temp. for 1 h. The reaction mixture was poured into ice-cold water and extracted with ethyl acetate (2×50 mL). The combined organic layer was washed successively with 0.2 N $H_2SO_4$, water and brine and then dried over sodium sulfate. The residue (350 mg) obtained after evaporation of the solvent was chromatographed over silica gel column using methanol and dichloromethane mixtures. The fractions eluted with 15% methanol/$CH_2Cl_2$ furnished 3-O-acetyl-11-keto-β-boswellic acid amide (325 mg). Melting point: 162-170° C., IR (KBr): 3465 (br), 2978, 2925, 2868, 1736, 1662, 1459, 1378, 1252, 1200, 1025 $cm^{-1}$; LC-MS (positive mode): m/z 512 $(M+H)^+$, 534 $(M+Na)^+$, 550 $(M+K)^+$, 1045 $(2M+Na)^+$.

EXAMPLE 20

N-(3-O-acetyl-11-keto-β-boswelloyl)-hydrazide (20): A mixture of 3-O-acetyl-11-keto-β-boswellic acid (450 mg, 0.88 mmol) and thionyl chloride (0.62 mL) was subjected to reflux in an oil bath. After 1 h, the excess reagent was removed and dried under reduced pressure to give the corresponding acid chloride. This crude acid chloride was dissolved in $CH_2Cl_2$ (3.0 mL) and treated slowly with hydrazine hydrate (265 mg, 5.3 mmol) at ice-cold temp. for 5 min. and the stirring was continued at the same temperature for 2 h. The reaction mixture was poured into ice-cold water and extracted with ethyl acetate (2×30 mL). The combined organic layer was washed with 0.2N $H_2SO_4$, water and brine, and dried over sodium sulfate. The solution was filtered and the solvent evaporated to give the hydrazide, 20 (390 mg, 85%). Melting point: 190-192° C.; $^1$HNMR ($CDCl_3$): δ 0.80 (3H, d; J=6.4 Hz, —$CH_3$), 0.83 (3H, s, —$CH_3$), 0.95 (3H, s, —$CH_3$), 1.10 (3H, s, —$CH_3$), 1.15 (3H, s, —$CH_3$), 1.20 (3H, s, —$CH_3$), 1.35 (3H, s, —$CH_3$), 2.09 (3H, s, $CH_3CO$—), 2.24-2.34 (1H, m), 2.41 (1H, s), 2.55 (1H, brd; 13.2 Hz), 3.86 (2H, brs, —CONHN$\underline{H}_2$), 5.34 (1H, brs, 3-H), 5.56 (1H, s, 12-H), 6.77 (1H, brs, —CON$\underline{H}$N$H_2$); IR (KBr): 3600-2400 (br), 2925, 1737, 1662, 1459, 1377, 1252, 1201, 1023, 879, 808 $cm^{-1}$; LC-MS (positive mode): m/z 527.6 $(M+H)^+$, 549.6 (M+Na), 1076.1 $(2M+Na)^+$.

EXAMPLE 21

N-(3-O-Acetyl-11-ketoboswelloyl)-ethylenediamine (21): A mixture of 3-O-acetyl-11-keto-β-boswellic acid (500 mg, 0.98 mmol) and thionyl chloride (0.7 mL, 9.4 mmol) was subjected to reflux on an oil bath. After 1 h, the excess reagent was removed and dried under reduced pressure to give the corresponding acid chloride. This crude acid chloride was dissolved in $CH_2Cl_2$ (4.0 mL) and treated slowly with ethylene diamine (351 mg, 5.85 mmol) at ice-cold temperature for 5 min. and the stirring was continued at the same temperature for 1 h. The reaction mixture was poured into ice-cold water and extracted with ethyl ether (2×30 mL). The combined organic layer was washed with 0.2N $H_2SO_4$, water and brine, and dried over sodium sulfate. The solution was filtered and the solvent evaporated. The residue (500 mg, yield 92%) was subjected to silica column chromatography using $CH_3OH$/$CH_2Cl_2$ mixtures. The fractions eluted with 10% $CH_3OH$/$CH_2Cl_2$ yielded pure N-(3-O-acetyl-11-keto-β-boswelloyl)-ethylenediamine (440 mg) as a white solid. Melting point: 198-202° C., $^1$HNMR ($CDCl_3$): δ 0.80 (3H, d; J=6.4 Hz, —$CH_3$), 0.82 (3H, s, —$CH_3$), 0.95 (3H, s, —$CH_3$), 1.12 (3H, s, —$CH_3$), 1.17 (3H, s, —$CH_3$), 1.19 (3H, s, —$CH_3$), 1.34 (3H, s, —$CH_3$), 2.09 (3H, s, $CH_3CO$—), 2.24-2.36 (1H, m), 2.41 (1H, s), 2.54 (1H, brd; 13.2 Hz), 2.87-2.96 (2H, m, —CONHCH$_2$C$\underline{H}_2$NH$_2$), 3.28-3.42 (2H, m, —CONHC$\underline{H}_2$CH$_2$NH$_2$), 5.33 (1H, brs, 3-H), 5.55 (1H, s, 12-H), 6.39 (1H, brs, —CON$\underline{H}$CH$_2$CH$_2$NH$_2$); IR (KBr): 3430 (br), 2976, 2925, 2867, 1734, 1659, 1521, 1458, 1376, 1252, 1199, 1023 $cm^{-1}$; LC-MS (positive mode): m/z 555 $(M+H)^+$, 1131 $(2M+Na)^+$.

EXAMPLE 22

N-(3-O-Acetyl-11-keto-β-boswelloyl)-2-aminoethanol (22): A mixture of 3-O-acetyl-11-keto-β-boswellic acid (500 mg, 0.98 mmol) and thionyl chloride (0.7 mL, 9.4 mmol) was subjected to reflux on an oil bath. After 1 h, the excess reagent was removed and dried under reduced pressure to give the corresponding acid chloride. This crude acid chloride was dissolved in $CH_2Cl_2$ (4.0 mL) and treated slowly with ethanol amine (350 μL, 5.86 mmol) at ice-cold temperature for 5 min. and the stirring was continued at the same temperature for 2 h. The reaction mixture was poured into ice-cold water and extracted with ethyl ether (2×30 mL). The combined organic layer was washed with 0.2 N $H_2SO_4$ (40 mL), water (40 mL) and brine (40 mL), and dried over sodium sulfate. The solution was filtered and the solvent evaporated. The residue (570 mg) was crystallized from $CH_2Cl_2$ to obtain pure N-(3-O-acetyl-11-keto-β-boswelloyl)-2-aminoethanol (480 mg, 89%) as a white solid. Melting point: 284-290° C., $^1$H NMR ($CDCl_3$): δ 0.81 (3H, d; J=6.4 Hz, —$CH_3$), 0.83 (3H, s, —$CH_3$), 0.95 (3H, s, —$CH_3$), 1.15 (3H, s, —$CH_3$), 1.17 (3H, s, —$CH_3$), 1.20 (3H, s, —$CH_3$), 1.35 (3H, s, —$CH_3$), 2.09 (3H, s, $CH_3CO$—), 2.26-2.36 (1H, m), 2.42 (1H, s), 2.56 (1H, br d; 13.2 Hz), 3.37-3.49 (2H, m, —CONHC$\underline{H}_2$CH$_2$OH), 3.67-3.80 (2H, m, —CONHCH$_2$C$\underline{H}_2$OH), 5.33 (1H, brs, 3-H), 5.56 (1H, s, 12-H), 6.00 (1H, brs, —CON$\underline{H}$CH$_2$CH$_2$OH); IR (KBr): 3430 (br), 2978, 2933, 1726, 1662, 1633, 1530, 1458, 1372, 1245, 1200, 1070, 1027, 991 $cm^{-1}$; LC-MS (positive mode): m/z 556 $(M+H)^+$, 578 $(M+Na)^+$, 594 $(M+K)^+$, 1133 $(2M+Na)^+$.

EXAMPLE 23

N-(3-O-Acetyl-11-keto-β-boswelloyl)-piperzine (23): A mixture of 3-O-acetyl-11-keto-β-boswellic acid (500 mg, 0.98 mmol) and thionyl chloride (0.7 mL, 9.4 mmol) was subjected to reflux on an oil bath. After 1 h, the excess reagent was removed and dried under reduced pressure to give the corresponding acid chloride. This crude acid chloride was dissolved in $CH_2Cl_2$ (4.0 mL) and treated slowly with piperzine (351 mg, 5.85 mmol) at ice-cold temperature for 5 min.

[Top of column 23, continuing description:]
ing point: 206-210° C.; $^1$HNMR ($CDCl_3$): δ 0.80 (3H, d; J=6.4 Hz, —$CH_3$), 0.82 (3H, s, —$CH_3$), 0.94 (3H, s, —$CH_3$), 1.02 (3H, s, —$CH_3$), 1.17 (3H, s, —$CH_3$), 1.19 (3H, s, —$CH_3$), 1.34 (3H, s, —$CH_3$), 2.09 (3H, s, —$COCH_3$), 2.41 (1H, s), 2.54 (1H, brd; 13.5 Hz), 2.91 (6H, s, 2×N—$CH_3$), 3.26-3.42 (2H, m, —OCH$_2$C$\underline{H}_2$N($CH_3$)$_2$), 4.46-4.56 (1H, m, —OC$\underline{H}_2$CH$_2$N($CH_3$)$_2$), 4.57-4.65 (1H, m, —OC$\underline{H}_2$CH$_2$N($CH_3$)$_2$), 5.28 (1H, br s, 3-H), 5.55 (1H, s, 12-H); IR (KBr): 3446 (br), 2978, 2926, 2868, 1736, 1660, 1461, 1382, 1250, 1113, $cm^{-1}$; LC-MS (positive mode): m/z 584 $(M+H)^+$.

and the stirring was continued at the same temperature for 2 h. The reaction mixture was poured into ice-cold water and extracted with ethyl ether (2×30 mL). The combined organic layer was washed with 0.2N $H_2SO_4$, water and brine, and dried over sodium sulfate. The solution was filtered and the solvent evaporated. The residue (620 mg) was subjected to silica column chromatography using $CH_3OH/CH_2Cl_2$ mixtures. The fractions eluted with 10% $CH_3OH/CH_2Cl_2$ yielded pure N-(3-O-acetyl-11-ketoboswelloyl)-piperzine (500 mg, 88%) as a white solid. Melting point: 180-184° C., $^1$HNMR ($CDCl_3$): δ 0.81 (3H, d; J=6.4 Hz, —$CH_3$), 0.83 (3H, s, —$CH_3$), 0.95 (3H, s, —$CH_3$), 1.225 (3H, s, —$CH_3$), 1.232 (3H, s, —$CH_3$), 1.25 (3H, s, —$CH_3$), 1.33 (3H, s, —$CH_3$), 2.11 (3H, s, $CH_3CO$—), 2.41 (1H, s), 2.54 (1H, brd; 13.4 Hz), 2.87-3.01 [4H, m, —CON($CH_2C\underline{H}_2)_2NH$], 3.57 [1H, br m, —CON($CH_2CH_2)_2N\underline{H}$], 3.58-3.68 [2H, m, —CON(C$\underline{H}_2CH_2)_2NH$], 3.68-3.79 [2H, m, —CON(C$\underline{H}CH_2)_2NH$], 5.55 (1H, s, 12-H), 5.55 (1H, br s, 3-H); IR (KBr): 3433 (br), 2982, 2925, 2863, 1737, 1657, 1457, 1377, 1247, 1209, 1021 $cm^{-1}$; LC-MS (positive mode): m/z 581 $(M+H)^+$, 1161 $(2M+H)^+$, 1183 $(2M+Na)^+$.

EXAMPLE 24

3-Acetoxy-11-keto-24-norurs-12-en-4-isocyanate (24): A solution of NaOH (0.066 g) in water (0.6 mL) was cooled to 0° C. and treated with bromine (0.022 mL). After 10 min, 3-O-acetyl-11-keto-β-boswellic acid amide (0.15 g) in acetone (0.5 mL) was added to the NaOBr solution and the mixture was heated at 70-75° C. for 45 min. The reaction mixture was diluted with ethyl ether (40 mL) and washed with water (20 mL) and brine (30 mL) and dried over $Na_2SO_4$. The solvent was evaporated and the residue was purified over silica gel using hexane/ethyl acetate mixtures. Fractions eluted with 5% and 10% ethyl acetate/hexane mixtures were monitored and those showing a yellow colored spot were combined and evaporated to give 3α-acetoxy-11-keto-24-norurs-12-en-4-isocyanate as a white solid (70 mg). Melting point: 170-176° C., IR (KBr): 2926, 2856, 2267, 1744, 1658, 1458, 1619, 1458, 1379, 1238, 1205, 1044 $cm^{-1}$; LC-MS (positive mode) m/z 510 $(M+H)^+$, 532 $(M+Na)^+$, 1041 $(2M+Na)^+$.

EXAMPLE 25

3α-Acetoxy-4-amino-11-keto-24-norurs-12-ene (25): A solution of NaOH (0.164 g) in water (0.8 mL) and dioxane (0.8 mL) was cooled to 0° C. and treated with bromine (0.060 mL). To the resulting NaOBr solution was added, after 10 min, 3-O-acetyl-11-keto-β-boswellic acid amide (0.4 g) in 1 mL dioxane and the mixture was heated at 65-75° C. for 2 h. The reaction mixture was poured into ice-water and the white precipitate was filtered, washed with water and dried under vacuum to obtain 3α-acetoxy-4-amino-11-keto-24-norurs-12-ene (250 mg). The mother liquor was extracted with dichloromethane (2×30 mL) and the organic layer was washed with water, brine and dried over $Na_2SO_4$. The solvent was evaporated and the residue was crystallized from hexane and ethyl acetate mixture to give a further quantity of 3α-acetoxy-4-amino-11-keto-24-norurs-12-ene (50 mg). Melting point: 212-216° C.; $^1$HNMR ($CDCl_3$): δ 0.83 (3H, d; J=7.0 Hz, —$CH_3$), 0.84 (3H, s, —$CH_3$), 0.97 (3H, d; J=7.1 Hz, —$CH_3$), 1.22 (3H, s, —$CH_3$), 1.32 (3H, s, 2×—$CH_3$), 1.37 (3H, s, —$CH_3$), 2.10 (3H, s, —$OCOC\underline{H}_3$), 2.45 (1H, s), 3.72 (2H, s), 4.61 (1H, br 3-H), 5.57 (1H, s, 12-H); IR (KBr): 3349, 2957, 2926, 2858, 2267, 1733, 1660, 1459, 1379, 1024, 804 $cm^1$; LC-MS (positive mode) m/z 484 $(M+H)^+$.

EXAMPLE 26

3α-Acetoxy-4-cyano-11-keto-24-norurs-12-ene (26): 3-O-Acetyl-11-ketoboswellic acid amide (200 mg, 0.39 mmol) in ethylene dichloride (2 mL) was treated with $SOCl_2$ (0.04 mL, 0.58 mmol) and the mixture was refluxed for 6 h. The mixture was poured into ice water and extracted with ethyl acetate (2×30 mL). The combined organic layer was washed with water and brine, and dried over $Na_2SO_4$. The solvent was evaporated and the residue (190 mg) was subjected to silica column chromatography using hexane/ethyl acetate mixtures. The fractions eluted with 10% hexane/ethyl acetate were evaporated to obtain 3α-acetoxy-4-cyano-11-keto-24-norurs-12-ene (140 mg, 72%). Melting point: 214-218° C.; $^1$HNMR ($CDCl_3$): δ 0.81 (3H, d; J=6.5 Hz, —$CH_3$), 0.84 (3H, s, —$CH_3$), 0.95 (3H, d; J=7.1 Hz, —$CH_3$), 1.24 (3H, s, —$CH_3$), 1.34 (3H, s, 2×—$CH_3$), 1.44 (3H, s, —$CH_3$), 2.10 (3H, s, —$OCOC\underline{H}_3$), 2.20 (1H, m), 2.40 (1H, s), 2.67 (1H, br d; 13.6 Hz), 5.11 (1H, br s, 3-H), 5.57 (1H, s, 12-H); IR ($CHCl_3$): 2924, 2858, 1744, 1663, 1453, 1383, 1232, 1027; LC-MS (positive mode) m/z 494 $(M+H)^+$, 516 $(M+Na)^+$, 532 $(M+K)^+$, 1009 $(2M+Na)^+$.

EXAMPLE 27

11-Hydroxy-β-boswellic acid (27): Lithium aluminum hydride (30 mg, 0.96 mmol) was dispersed in THF and cooled in ice water bath. A solution of 11-keto-β-boswellic acid (150 mg, 0.32 mmol) in THF (2 mL) was slowly added to the above dispersion and the stirring continued in the ice water bath for 2 h. The reaction mixture was diluted with ethyl acetate (2 mL) and after 5 minutes it was poured in to ice water. The mixture was carefully neutralized with 1 N HCl and extracted with ethyl acetate (3×25 mL). The combined organic layer was washed with water, brine, dried over $Na_2SO_4$ and evaporated. The residue was purified on silica column using hexane and ethyl acetate mixtures. The fractions eluted with 25% ethyl acetate/hexane mixture yielded 11-hydroxy-β-boswellic acid (70 mg). Melting point: 152-160° C., $^1$HNMR ($CDCl_3$): δ 0.80 (3H, d; J=5.6 Hz, —$CH_3$), 0.85 (3H, s, —$CH_3$), 0.93 (3H, s, —$CH_3$), 1.07 (3H, s, —$CH_3$), 1.10 (3H, s, —$CH_3$), 1.18 (3H, s, —$CH_3$), 1.36 (3H, s, —$CH_3$), 1.96-2.08 (1H, m), 2.15 (1H, brd; J=13.3), 2.19-2.31 (1H, m), 4.08 (1H, br s), 4.26 1H, dd; J=9.1 and 2.9 Hz, 11-H), 5.18 (1H, d; J=2.9 Hz, 12-H); FT-IR (neat): 3390, 2921, 2860, 1696, 1451, 1379, 1246, 1001 $cm^1$. LC-MS (negative mode): 471 $(M–H)^-$.

5-LOX Assay

The AKBA analogs were screened for their 5-Lipoxygenase inhibitory potential using calorimetric method of Craig A. Gay et al (*Anal Biochem.,* 304, 42-46, 2002). The assay mixture contained 50 mM phosphate buffer pH 6.3, 5-Lipoxygenase, various concentrations of test substances and linoleic acid in a total volume of 0.5 mL after 5 min incubation of above reaction mixture 0.5 ml ferric xylenol orange reagent was added and OD was measured after two minutes at 585 nm using spectrophotometer (varian). Controls were run along with test in a similar manner except using vehicle instead of test substance solution. Percent inhibition was calculated by comparing absorbance of test with that of control Brine Shrimp Lethality Assay Brine shrimp lethality (BSL) assay is a simple bench top bioassay developed by McLaughlin, et. al. (*Studies in Natural Product Chemistry,* 9, page 383, 1991 and *Am. Chem. Soc. Symp. Series,* 534, page 114, 1992) and the results obtained by this assay have been reported to be corroborative with the cytotoxicities determined in 9KB and 9PS cells. The procedure involves hatching *Artemia salina* cysts in a cone shaped vessel and collecting active nauplii after 48 hr and treating with known concentrations of test substances and vehicle (control) in tubes each tube containing 10 nauplii and checking viability/mortality after 24 hr. Percentage lethality was calculated by comparing mean values of control and test sets of three tubes each. $LC_{50}$ values were obtained from the graph plotted micro molar concentration against percent lethality.

The new analogs exhibited 5-Lipoxigenase inhibitory activities. The 5-Lipoxigenase inhibitory activities of these analogs are summarized in table I. Consistent with the antiproliferative actions reported for known boswellic acid compounds, the analogs of the present invention inhibited the growth of Brine Shrimp in cultures, which is a possible indication for their antitumor activity. The Brine Shrimp inhibitory activity of these compounds is summarized in table II.

TABLE I

5-LO inhibitory activity of new boswellic acid analogs

| Str. # | Name | % inhibition @ 100 μM | % inhibition @ 250 μM |
|---|---|---|---|
| B2 | 3-O-Acetyl-11-keto-β-boswellic acid (AKBA) | 18.7 | 31 |
| 1 | 3-O-Formyl-11-keto-β-boswellic acid | | 5.5 |
| 2 | 3-O-(Chloroacetyl)-11-keto-β-boswellic acid | | 3.12 |
| 3 | 3-O-(5'-O-Methylgalloyl)-11-keto-β-boswellic acid | 27.4 | |
| 4 | 3-O-Succinyl-11-keto-β-boswellic Acid | | 41.1 |
| 5 | 3-O-[8',9'-Dihydro-4'-hydroxycinnamoyl]-11-keto-β-boswellic acid | | N/A |
| 6 | 3-O-[4'-Hydroxycinnamoyl]-11-keto-β-boswellic acid | | 11.3 |
| 7 | 3-O-(3',4'-Dimethoxycinnamoyl)-11-keto-β-boswellic acid | | 17.8 |
| 8 | 3-O-(3',4'-Dihydroxy-5'-methoxycinnamoyl)-11-keto-β-boswellic acid | | 8.1 |
| 9 | Methyl 3-O-(N-Boc-glycyl)-11-keto-β-boswellate | | 16.7 |
| 10 | 3-O-Glycyl-11-keto-β-boswellic acid hydrochloride | 23.9 | |
| 11 | 3-O-Alanyl-11-keto-β-boswellic acid hydrochloride | 33.6 | |
| 12 | Methyl 3-β-hydroxy-11-ketours-12-en-24-oate | | 0.37 |
| 13 | Methyl-3-α-bromo-11-keto-12-ursen-24-oate | | 17.6 |
| 14 | Methyl 3-α-cyano-11-keto-12-ursen-24-oate | | 3.71 |
| 15 | Methyl 3-α-thiohydroxy-11-ketours-12-en-24-oate | | 53.1 |
| 16 | Methyl 3, 11-diketours-12-en-24-oate 3-oxime | | 41.6 |
| 17 | 3-Acetoxy-11-keto-24-norurs-12-ene | | 0 |
| 18 | (2'-N,N-Dimethylaminoethyl) 3-O-acetyl-11-keto-β-boswellate | 25.4 | |
| 19 | 3-O-Acetyl-11-keto-β-boswellic acid amide | | 35.8 |
| 20 | N-(3-O-Acetyl-11-keto-β-boswelloyl)-hydrazide | | 54.3 |
| 21 | N-(3-O-Acetyl-11-keto-β-boswelloyl)-ethylenediamine | | 76.6 |
| 22 | N-(3-O-Acetyl-11-keto-β-boswelloyl)-2-aminoethanol | | 10.4 |
| 23 | N-(3-O-Acetyl-11-keto-β-boswelloyl)-piperzine | 34.9 | |
| 24 | 3-Acetoxy-11-keto-24-norurs-12-en-4-isocyanate | | 0 |
| 25 | 3-Acetoxy-4-amino-11-keto-24-norurs-12-ene | | 60.5 |
| 26 | 3-Acetoxy-4-cyano-11-keto-24-norurs-12-ene | | 9.8 |
| 27 | 11-Hydroxy-β-boswellic acid | | 12.2 |

TABLE II

Brine Shrimp Lethality Assay of AKBA Analogs

| Str. # | Name | $LD_{50}$ in mcM |
|---|---|---|
| B2 | 3-O-Acetyl-11-keto-β-boswellic acid (AKBA) | 5.5 |
| 1 | 3-O-Formyl-11-keto-β-boswellic acid | 55.0 |
| 2 | 3-O-(Chloroacetyl)-11-keto-β-boswellic acid | 98.0 |
| 3 | 3-O-(5'-O-Methylgalloyl)-11-keto-β-boswellic acid | 33.0 |
| 4 | 3-O-Succinyl-11-keto-β-boswellic Acid | 69.0 |
| 5 | 3-O-[8',9'-Dihydro-4'-hydroxycinnamoyl]-11-keto-β-boswellic acid | N/A |
| 6 | 3-O-[4'-Hydroxycinnamoyl]-11-keto-β-boswellic acid | 6.0 |
| 7 | 3-O-(3',4'-Dimethoxycinnamoyl)-11-keto-β-boswellic acid | 6.2 |
| 8 | 3-O-(3',4'-Dihydroxy-5'-methoxycinnamoyl)-11-keto-β-boswellic acid | 12.0 |
| 9 | Methyl 3-O-(N-Boc-glycyl)-11-keto-β-boswellate | >100 |
| 10 | 3-O-Glycyl-11-keto-β-boswellic acid hydrochloride | 12.0 |
| 11 | 3-O-Alanyl-11-keto-β-boswellic acid hydrochloride | 29.0 |
| 12 | Methyl 3-β-hydroxy-11-ketours-12-en-24-oate | >100 |
| 13 | Methyl-3-α-bromo-11-keto-12-ursen-24-oate | >100 |
| 14 | Methyl 3-α-cyano-11-keto-12-ursen-24-oate | >100 |
| 15 | Methyl 3-α-thiohydroxy-11-ketours-12-en-24-oate | 5.2 |
| 16 | Methyl 3, 11-diketours-12-en-24-oate 3-oxime | >100 |
| 17 | 3-Acetoxy-11-keto-24-norurs-12-ene | >100 |
| 18 | (2'-N,N-Dimethylaminoethyl) 3-O-acetyl-11-keto-β-boswellate | >100 |
| 19 | 3-O-Acetyl-11-keto-β-boswellic acid amide | 4.6 |
| 20 | N-(3-O-Acetyl-11-keto-β-boswelloyl)-hydrazide | 2.3 |
| 21 | N-(3-O-Acetyl-11-keto-β-boswelloyl)-ethylenediamine | 71 |

TABLE II-continued

Brine Shrimp Lethality Assay of AKBA Analogs

| Str. # | Name | $LD_{50}$ in mcM |
| --- | --- | --- |
| 22 | N-(3-O-Acetyl-11-keto-β-boswelloyl)-2-aminoethanol | >100 |
| 23 | N-(3-O-Acetyl-11-keto-β-boswelloyl)-piperzine | 0.88 |
| 24 | 3-Acetoxy-11-keto-24-norurs-12-en-4-isocyanate | >100 |
| 25 | 3-Acetoxy-4-amino-11-keto-24-norurs-12-ene | 6.0 |
| 26 | 3-Acetoxy-4-cyano-11-keto-24-norurs-12-ene | >100 |
| 27 | 11-Hydroxy-β-boswellic acid | 28.3 |

We claim:

1. A compound of the formula I

I wherein $R_1$, $R_2$, $R_3$, $R_4$ and $R_5$ are:
$R_1$=OCOCH$_2$Cl, $R_2$=H, $R_3$=COOH, $R_4$ and $R_5$=O;
$R_1$=5'-O-methylgalloyloxy, $R_2$=H, $R_3$=COOH, $R_4$ and $R_5$=O;
$R_1$=OCOCH$_2$CH$_2$COOH, $R_2$=H, $R_3$=COOH, $R_4$ and $R_5$=O;
$R_1$=8',9'-Dihydro-4'-hydroxycinnamoyloxy, $R_2$=H, $R_3$=COOH, $R_4$ and $R_5$=O;
$R_1$=4'-Hydroxycinnamoyloxy, $R_2$=H, $R_3$=COOH, $R_4$ and $R_5$=O;
$R_1$=3',4'-Dimethoxycinnamoyloxy, $R_2$=H, $R_3$=COOH, $R_4$ and $R_5$=O;
$R_1$=3',4'-Dihydroxy-5'-methoxycinnamoyloxy, $R_2$=H, $R_3$=COOH, $R_4$ and $R_5$=O;
$R_1$=OCOCH$_2$NH(tert-BOC), $R_2$=H, $R_3$=COOCH$_3$, $R_4$ and $R_5$=O;
$R_1$=OCOCH$_2$NH$_2$HCl, $R_2$=H, $R_3$=COOH, $R_4$ and $R_5$=O;
$R_1$=OCOCH(CH$_3$)NH$_2$HCl, $R_2$=H, $R_3$=COOH, —$R_4$ and $R_5$=O;
$R_1$=H, $R_2$=Br, $R_3$=COOCH$_3$, $R_4$ and $R_5$=O;
$R_1$=CN, $R_2$=H, $R_3$=COOCH$_3$, $R_4$ and $R_5$=O;
$R_1$=SH, $R_2$=H, $R_3$=COOCH$_3$, $R_4$ and $R_5$=O;
$R_1$ and $R_2$=N(OH), $R_3$=COOCH$_3$, $R_4$ and $R_4$=O;
$R_1$ and $R_2$=OCOCH$_3$, $R_3$=H, $R_4$ and $R_5$=O;
$R_1$=OCOCH$_3$, $R_2$=H, $R_3$=COOCH$_2$CH$_2$N(CH$_3$)$_2$, $R_4$ and $R_5$=O;
$R_1$=OCOCH$_3$, $R_2$=H, $R_3$=CONH$_2$, $R_4$ and $R_5$=O;
$R_1$=OCOCH$_3$, $R_2$=H, $R_3$=CONHNH$_2$, $R_4$ and $R_5$=O;
$R_1$=OCOCH$_3$, $R_2$=H, $R_3$=CONHCH$_2$CH$_2$NH$_2$, $R_4$ and $R_5$=O;
$R_1$=OCOCH$_3$, $R_2$=H, $R_3$=CONHCH$_2$CH$_2$OH, $R_4$ and $R_5R_4$=O;
$R_1$=OCOCH$_3$, $R_2$=H, $R_3$=CON(CH$_2$CH$_2$)$_2$NH, $R_4$ and $R_5$=O;
$R_1$=OCOCH$_3$, $R_2$=H, $R_3$=NCO, $R_4$ and $R_5$=O;
$R_1$=OCOCH$_3$, $R_2$=H, $R_3$=NH$_2$, $R_4$ and $R_5$=O; or
$R_1$=OCOCH$_3$, $R_2$=H, $R_3$=CN, $R_4$ and $R_5$=O;

2. The compound of claim 1, wherein $R_1$ is chloroacetoxy group, $R_2$ is H, $R_3$ is carboxylic acid group and $R_4$ and $R_5$ taken together form a keto group, said compound represented by structural formula 3. The compound claim 1, wherein $R_1$ is 5'-O-methyl galloyloxy group, $R_2$ is H, $R_3$ is carboxylic acid group and $R_4$ and $R_5$ taken together form a keto group, said compound represented by structural formula 4. The compound of claim 1, wherein $R_1$ is succinyloxy (OCOCH$_2$CH$_2$COOH) group, $R_2$ is H, $R_3$ is carboxylic acid group, and $R_4$ and $R_5$ taken together form a keto group, said compound represented by structural formula

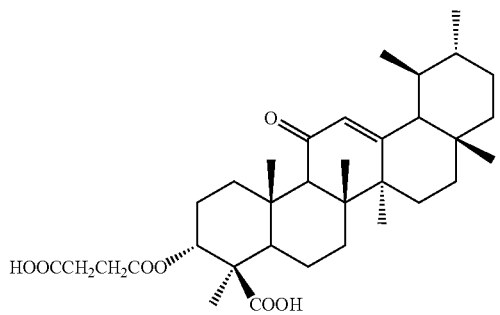

5. The compound of claim 1, wherein $R_1$ is 8',9'-dihydro-4'-hydroxycinnamoyloxy group, $R_2$ is H, $R_3$ is carboxylic acid group and $R_4$ and $R_5$ taken together form a keto group, said compound represented by structural formula

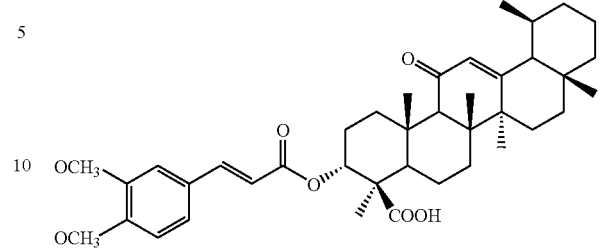

8. The compound of claim 1, wherein $R_1$ is 3',4'-dihydroxy-5'-methoxycinnamoyloxy group, $R_2$ is H; $R_3$ is carboxylic acid group and $R_4$ and $R_5$ taken together to form a keto group, said compound represented by structural formula

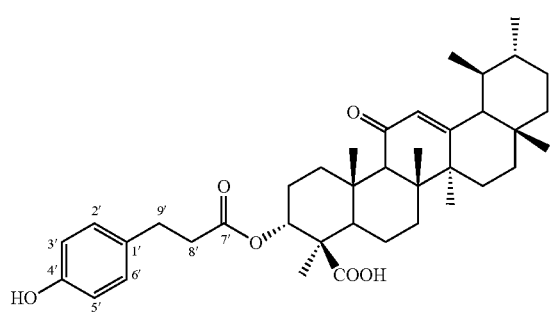

6. The compound of claim 1, wherein $R_1$ is 4'-hydroxy cinnamoyloxy group, $R_2$ is H, $R_3$ is carboxylic acid group and $R_4$ and $R_5$ taken together form a keto group, said compound represented by structural formula

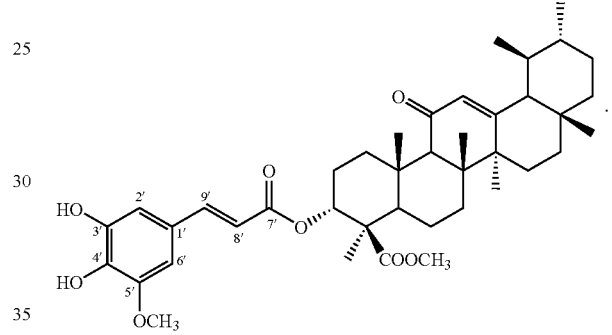

9. The compound of claim 1, where in $R_1$ is $OCOCH_2NH$ (tert-BOC) group, $R_2$ is H, $R_3$ is $COOCH_3$ and $R_4$ and $R_5$ taken together to form a keto group, as represented by the structural formula

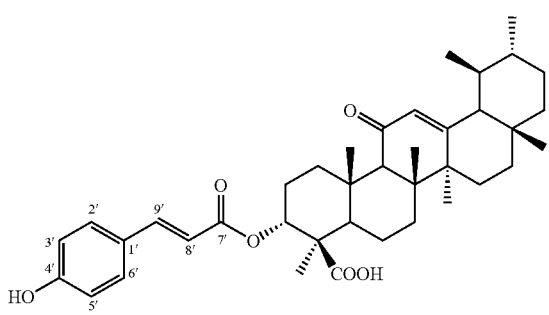

7. The compound of claim 1, wherein $R_1$ is 3',4'-dimethoxycinnamoyl group, $R_2$ is H, $R_3$ is carboxylic group, $R_4$ and $R_5$ taken together form a keto group, said compound represented by structural formula

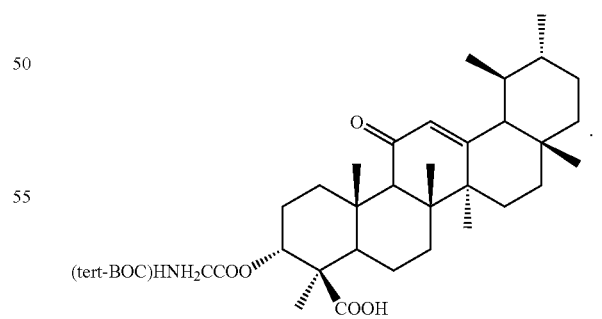

10. The compound of claim 1, wherein $R_1$ is $OCOCH_2NH_2HCl$ group, $R_2$ is H, $R_3$ is carboxylic acid group and $R_4$ and $R_5$ taken together to form a keto group, as represented by the structural formula

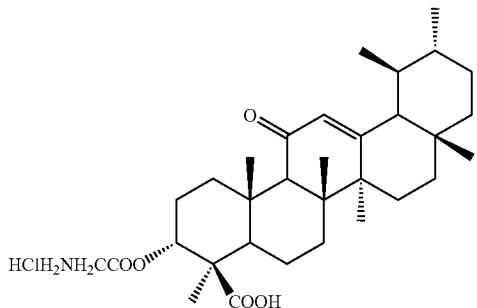

11. The compound of claim 1, where in $R_1$ is OCOCH($CH_3$)$NH_2$HCl group, $R_2$ is H, $R_3$ is carboxylic acid group and $R_4$ and $R_5$ taken together to form a keto group, as represented by the structural formula

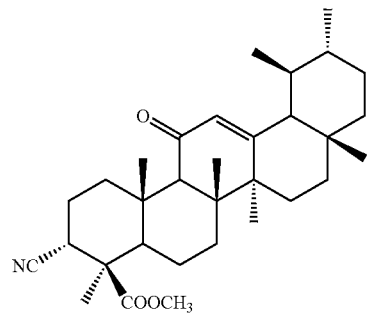

14. The compound of claim 1, where in $R_1$ is SH, $R_2$ is H, $R_3$ is COOCH$_3$ and $R_4$ and $R_5$ taken together to form a keto group, as represented by the structural formula

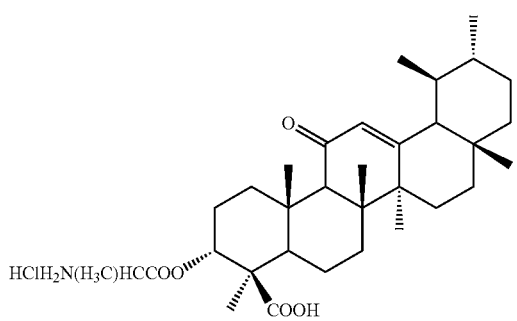

12. The compound of claim 1, where in $R_1$ is H, $R_2$ is Br, $R_3$ is COOCH$_3$ and $R_4$ and $R_5$ taken together to form a keto group, as represented by the structural formula

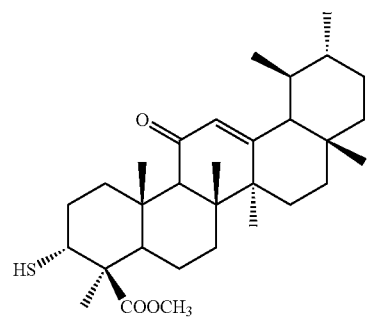

15. The compound of claim 1, where in $R_1$ and $R_2$ are taken together to form oximino [:N(OH)] group, $R_3$ is COOCH$_3$ and $R_4$ and $R_5$ taken together to form a keto group, as represented by the structural formula

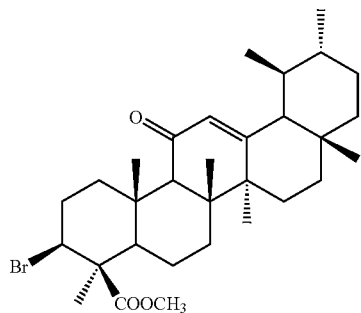

13. The compound of claim 1, where in $R_1$ is CN, $R_2$ is H, $R_3$ is COOCH$_3$ and $R_4$ and $R_5$ taken together to form a keto group, as represented by the structural formula

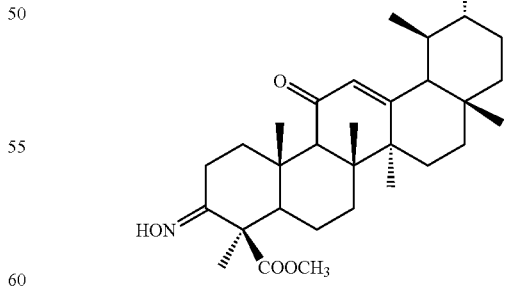

16. The compound of claim 1, where in $R_1$ and $R_2$ are OCOCH$_3$ and H, $R_3$ is H and $R_4$ and $R_5$ taken together to form a keto group, as represented by the structural formula

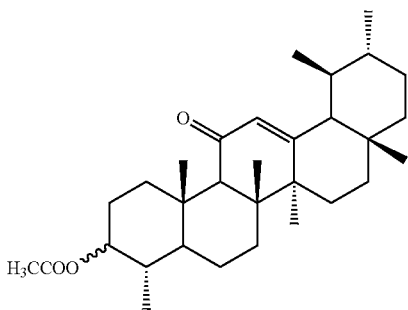

17. The compound of claim 1, where in $R_1$ is $OCOCH_3$, $R_2$ is H, $R_3$ is $COOCH_2CH_2N(CH_3)_2$ and $R_4$ and $R_5$ taken together to form a keto group, as represented by the structural formula

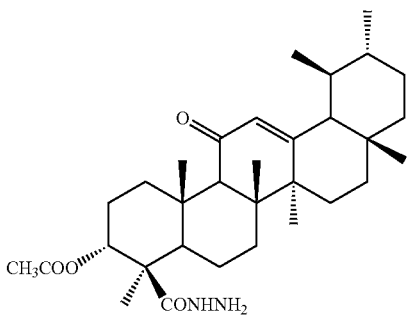

20. The compound of claim 1, where in $R_1$ is $OCOCH_3$, $R_2$ is H, $R_3$ is $CONHNH_2$ and $R_4$ and $R_5$ taken together to form a keto group, as represented by the structural formula

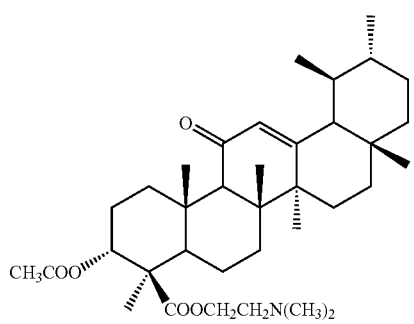

18. compound of claim 1, where in $R_1$ is $OCOCH_3$, $R_2$ is H, $R_3$ is $CONH_2$ and $R_4$ and $R_5$ taken together to form a keto group, as represented by the structural formula

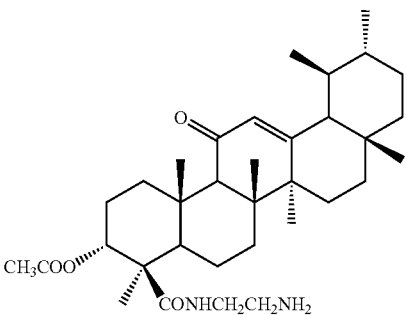

21. The compound of claim 1, where in $R_1$ is $OCOCH_3$, $R_2$ is H, $R_3$ is $CONHCH_2CH_2NH_2$ and $R_4$ and $R_5$ taken together to form a keto group, as represented by the structural formula

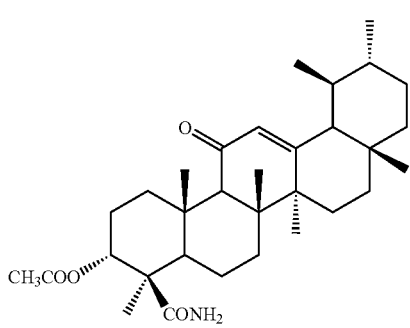

19. The compound of claim 1, where in $R_1$ is $OCOCH_3$, $R_2$ is H, $R_3$ is $CONHNH_2$ and $R_4$ and $R_5$ taken together to form a keto group, as represented by the structural formula

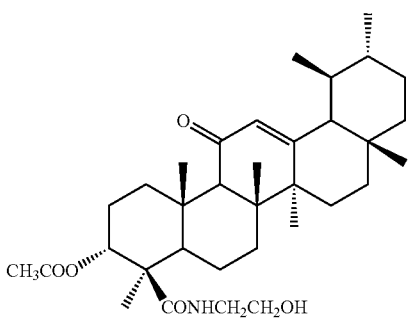

22. The compound of claim 1, where in $R_1$ is $OCOCH_3$, $R_2$ is H, $R_3$ is $CON(CH_2CH_2)_2NH$, and $R_4$ and $R_5$ taken together to form a keto group, as represented by the structural formula

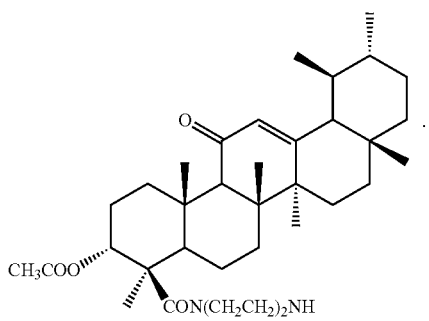

23. The compound of claim 1, where in $R_1$ is $OCOCH_3$, $R_2$ is H, $R_3$ is NCO and $R_4$ and $R_5$ taken together to form a keto group, as represented by the structural formula

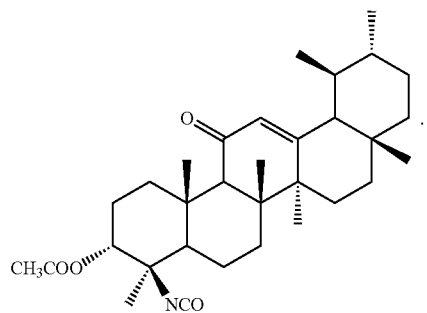

24. The compound of claim 1, where in $R_1$ is $OCOCH_3$, $R_2$ is H, $R_3$ is $NH_2$ and $R_4$ and $R_5$ taken together to form a keto group, as represented by the structural formula

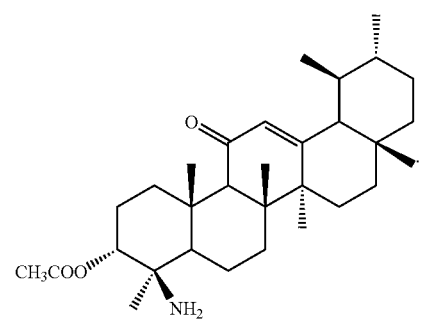

25. The compound of claim 1, where in $R_1$ is $OCOCH_3$, $R_2$ is H, $R_3$ is CN and $R_4$ and $R_5$ taken together to form a keto group, as represented by the structural formula

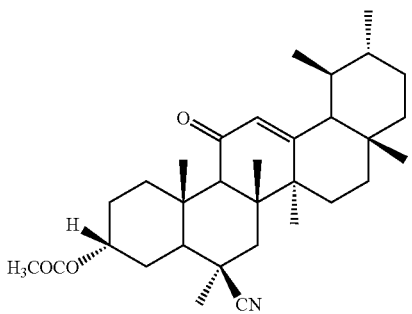

26. A process for preparing compounds represented by the formula I

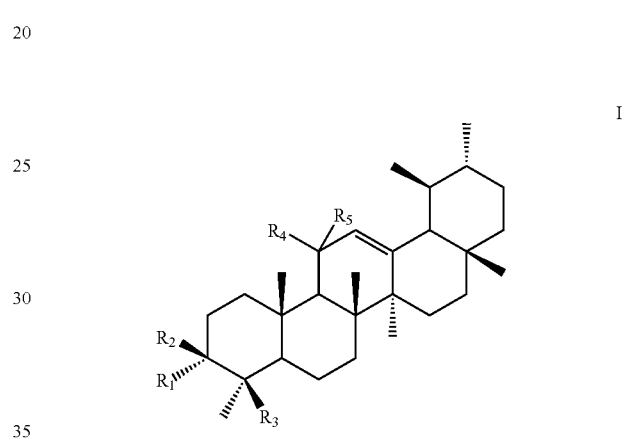

wherein $R_1$, $R_2$, $R_3$, $R_4$ and $R_5$ are:

$R_1$=$OCOCH_2Cl$, $R_2$=H, $R_3$=COOH, $R_4$ and $R_5$=O;

$R_1$=5'-O-methylgalloyloxy, $R_2$=H, $R_3$=COOH, $R_4$ and $R_5$=O;

$R_1$=$OCOCH_2CH_2COOH$, $R_2$=H, $R_3$=COOH, $R_4$ and $R_5$=O;

$R_1$=8', 9'-Dihydro-4'-hydroxycinnamoyloxy, $R_2$=H, $R_3$=COOH, $R_4$ and $R_5$=O;

$R_1$=4'-Hydroxycinnamoyloxy, $R_2$=H, $R_3$=COOH, $R_4$ and $R_5$=O;

$R_1$=3',4'-Dimethoxycinnamoyloxy, $R_2$=H, $R_3$=COOH, $R_4$ and $R_5$=O;

$R_1$=3',4'-Dihydroxy-5'-methoxycinnamoyloxy, $R_2$=H, $R_3$=COOH, $R_4$ and $R_5$=O;

$R_1$=$OCOCH_2NH(tert-BOC)$, $R_2$=H, $R_3$=$COOCH_3$, $R_4$ and $R_5$=O;

$R_1$=$OCOCH_2NH_2HCl$, $R_2$=H, $R_3$=COOH, $R_4$ and $R_5$=O; or $R_1$=$OCOCH(CH_3)NH_2HCl$, $R_2$=H, $R_3$=COOH, $R_4$ and $R_5$=O;

comprising the step of coupling 3-keto boswellic acid (KBA) or its ester with an organic acid in the presence of 1,3-dicyclohexyl carbodimide and 4-(dimethyl amino) pyridine as coupling agents.

27. A process for preparing compounds represented by the formula I

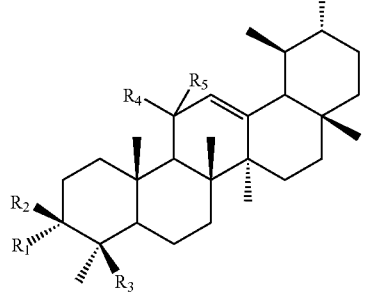

wherein $R_1$, $R_2$, $R_3$, $R_4$ and $R_5$ are:
- $R_1$=H, $R_2$=Br, $R_3$=COOCH$_3$, $R_4$ and $R_5$=O;
- $R_1$=CN, $R_2$=H, $R_3$=COOCH$_3$, $R_4$ and $R_5$=O; or
- $R_1$=SH, $R_2$=H, $R_3$=COOCH$_3$, $R_4$ and $R_5$=O;

comprising the steps of treating methyl ester of 3 keto boswellic acid with phosphorus tribromide to displace the 3αOH group by Br and further treating the same with a nucleophillic agent to displace the Br group with SH or CN.

28. A process for preparing compounds represented by the formula I

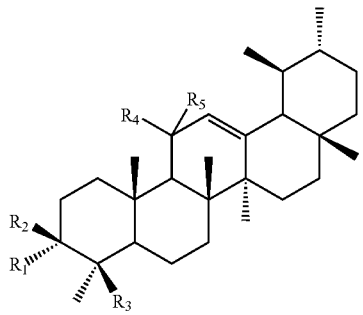

wherein $R_1$, $R_2$, $R_3$, $R_4$ and $R_5$ are;
- $R_1$=OCOCH$_3$, $R_2$=H, $R_3$=CONH$_2$, $R_4$ and $R_5$=O;
- $R_1$=OCOCH$_3$, $R_2$=H, $R_3$=CONHNH$_2$, $R_4$ and $R_5$=O;
- $R_1$=OCOCH$_3$, $R_2$=H, $R_3$=CONHCH$_2$CH$_2$NH$_2$, $R_4$ and $R_5$=O;
- $R_1$=OCOCH$_3$, $R_2$=H, $R_3$=CONHCH$_2$CH$_2$OH, $R_4$ and $R_4$=O; and
- $R_1$=OCOCH$_3$, $R_2$=H, R3=CON(CH$_2$CH$_2$)$_2$NH, $R_4$ and $R_5$=O;

comprising the step of treating the acid chloride of 3-O-acetyl-11-keto-β-boswellic acid with excess of amine in a solvent medium.

29. A pharmaceutical composition comprising at least one compound as claimed in claim 1 in a pharmaceutically acceptable carrier.

30. The pharmaceutical composition as claimed in claim 29, wherein said carrier is an aqueous or non-aqueous carrier.

* * * * *